(12) United States Patent
McConnell et al.

(10) Patent No.: US 7,628,772 B2
(45) Date of Patent: Dec. 8, 2009

(54) RESERVOIR CONNECTOR

(75) Inventors: Susan McConnell, Woodland Hills, CA (US); Randy W. Adair, Valencia, CA (US); Sheldon Moberg, Granada Hills, CA (US); Chad Srisathapat, Sun Valley, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 162 days.

(21) Appl. No.: 10/884,609

(22) Filed: Jul. 2, 2004

(65) Prior Publication Data

US 2004/0243065 A1    Dec. 2, 2004

Related U.S. Application Data

(63) Continuation of application No. 09/974,312, filed on Oct. 10, 2001, now abandoned, which is a continuation-in-part of application No. 09/428,818, filed on Oct. 28, 1999, now Pat. No. 6,585,695.

(60) Provisional application No. 60/106,237, filed on Oct. 29, 1998.

(51) Int. Cl.
*A61M 5/178* (2006.01)
*A61M 5/00* (2006.01)
*A61M 25/00* (2006.01)
*A61M 25/16* (2006.01)

(52) U.S. Cl. .................... 604/183; 604/181; 604/187; 604/533; 604/523; 604/535

(58) Field of Classification Search ................. 604/183, 604/181, 187, 533, 82, 87, 523, 535, 905, 604/240, 241
See application file for complete search history.

(56) References Cited

U.S. PATENT DOCUMENTS

| 3,623,474 A | 11/1971 | Hellman et al. |
| 3,701,345 A | 10/1972 | Hellman et al. |
| 4,084,588 A | 4/1978 | Koenig |
| 4,267,836 A | 5/1981 | Whitney et al. |
| 4,278,188 A | 7/1981 | Stephenson et al. |
| 4,444,546 A | 4/1984 | Pazemenas |
| 4,468,221 A | 8/1984 | Mayfield |
| 4,562,751 A | 1/1986 | Nason et al. |

(Continued)

FOREIGN PATENT DOCUMENTS

DE    2240694    8/1972

(Continued)

*Primary Examiner*—Jacqueline F. Stephens
(74) *Attorney, Agent, or Firm*—Gates & Cooper LLP

(57) ABSTRACT

Apparatuses and methods for a connection interface between a reservoir or syringe, infusion set tubing, and an infusion pump are provided. A base is provided which is adapted to receive a reservoir and engage a cap. A piercing member, such as a needle, is disposed in the interior of the cap in such a manner that the needle is separated from the reservoir septum when the base is in a first detent position, and the needle pierces a reservoir septum when the base is in a second detent position. When the reservoir, the base and the cap are connected to form an integrated unit, this unit is then capable of being inserted and secured in the infusion pump housing. In some embodiments, an integral connector couples directly to the reservoir.

44 Claims, 19 Drawing Sheets

U.S. PATENT DOCUMENTS

| | | | |
|---|---|---|---|
| 4,564,054 A | 1/1986 | Gustavsson |
| 4,576,211 A | 3/1986 | Valentini et al. |
| 4,601,491 A | 7/1986 | Bell, Jr. et al. |
| 4,610,469 A | 9/1986 | Wolff-Mooij |
| 4,619,646 A | 10/1986 | Hernandez et al. |
| 4,678,408 A | 7/1987 | Nason et al. |
| 4,685,903 A | 8/1987 | Cable et al. |
| 4,744,790 A | 5/1988 | Jankowski et al. |
| 4,747,824 A | 5/1988 | Spinello |
| 4,749,109 A | 6/1988 | Kamen |
| 4,834,744 A | 5/1989 | Ritson |
| 4,936,833 A | 6/1990 | Sams |
| 4,952,205 A | 8/1990 | Mauerer et al. |
| 5,062,832 A | 11/1991 | Seghi |
| 5,080,653 A | 1/1992 | Voss et al. |
| 5,087,250 A | 2/1992 | Lichte et al. |
| 5,097,122 A | 3/1992 | Colman et al. |
| 5,100,394 A | 3/1992 | Dudar et al. |
| 5,121,019 A | 6/1992 | Pradler |
| 5,137,524 A | 8/1992 | Lynn et al. |
| 5,188,610 A | 2/1993 | Rains |
| 5,201,717 A | 4/1993 | Wyatt et al. |
| 5,219,099 A | 6/1993 | Spence et al. |
| 5,254,096 A | 10/1993 | Rondelet et al. |
| 5,279,569 A | 1/1994 | Neer et al. |
| 5,292,306 A | 3/1994 | Wynkoop et al. |
| 5,295,657 A | 3/1994 | Atkinson |
| D347,894 S | 6/1994 | Hansen et al. |
| 5,330,450 A | 7/1994 | Lopez |
| 5,334,179 A | 8/1994 | Poli et al. |
| 5,374,256 A | 12/1994 | Kriesel |
| 5,389,078 A | 2/1995 | Zalesky et al. |
| 5,423,753 A | 6/1995 | Fowles et al. |
| 5,466,218 A | 11/1995 | Srisathapat et al. |
| 5,505,709 A | 4/1996 | Funderburk et al. |
| 5,545,152 A | 8/1996 | Funderburk et al. |
| 5,549,574 A | 8/1996 | Townsend |
| 5,554,134 A | 9/1996 | Bonnichsen |
| 5,599,323 A | 2/1997 | Bonnichsen et al. |
| 5,611,785 A | 3/1997 | Mito et al. |
| D380,262 S | 6/1997 | Van Funderburk et al. |
| 5,637,095 A | 6/1997 | Nason et al. |
| 5,647,853 A | 7/1997 | Feldmann et al. |
| 5,722,545 A | 3/1998 | Rinne |
| 5,779,675 A | 7/1998 | Reilly et al. |
| 5,810,792 A | 9/1998 | Fangrow et al. |
| 5,817,082 A | 10/1998 | Niedospial, Jr. et al. |
| 5,871,500 A | 2/1999 | Jepson et al. |
| 5,895,383 A | 4/1999 | Niedospial, Jr. |
| 5,947,935 A | 9/1999 | Rhinehart et al. |
| 5,989,215 A * | 11/1999 | Delmotte et al. ............... 604/82 |
| 6,090,082 A | 7/2000 | King et al. |
| 6,488,650 B1 * | 12/2002 | Epstein et al. ................. 604/82 |

FOREIGN PATENT DOCUMENTS

| | | |
|---|---|---|
| DE | 9013145 U1 | 11/1990 |
| EP | 0544653 | 1/1989 |
| EP | 0453212 | 10/1991 |
| FR | 2628639 | 9/1989 |
| JP | 5-74545 | 10/1993 |
| WO | WO 91/16938 | 11/1991 |
| WO | 9800157 | 10/1998 |
| WO | WO 02/076527 A2 | 10/2002 |

* cited by examiner

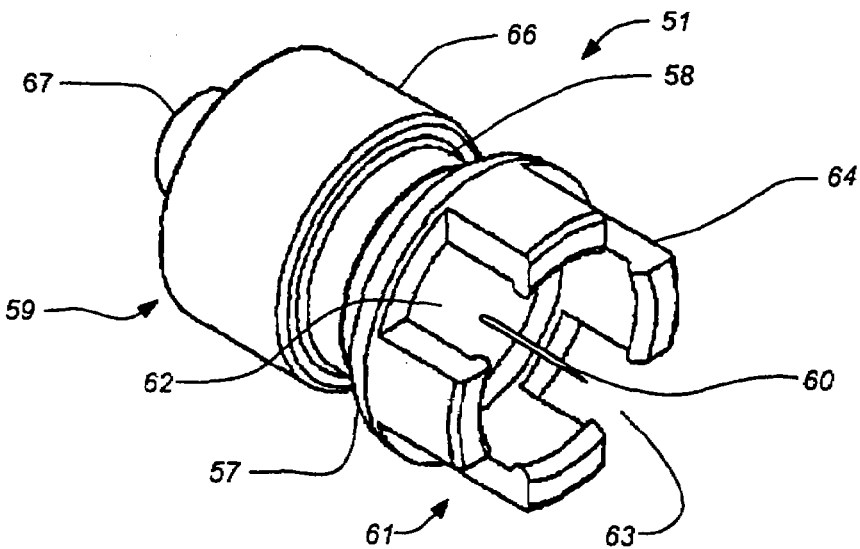
FIG. 16A
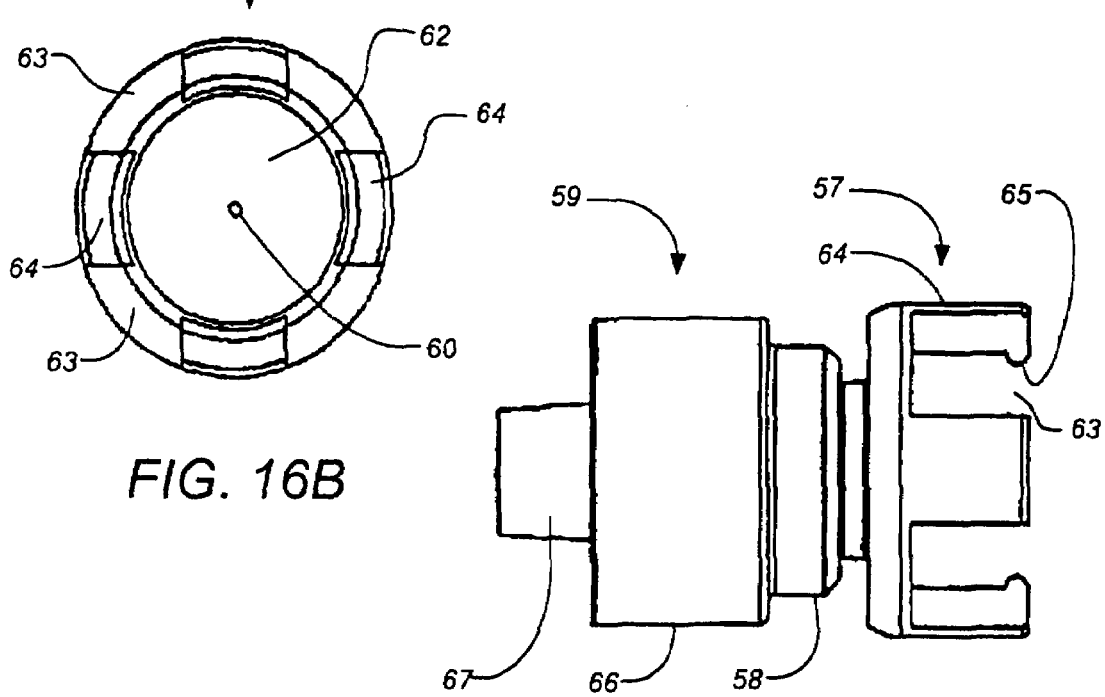
FIG. 16B
FIG. 16C

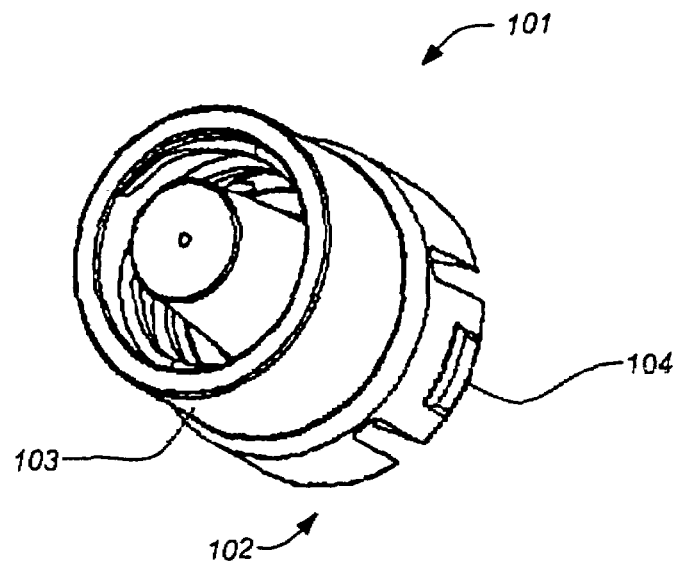
FIG. 18A
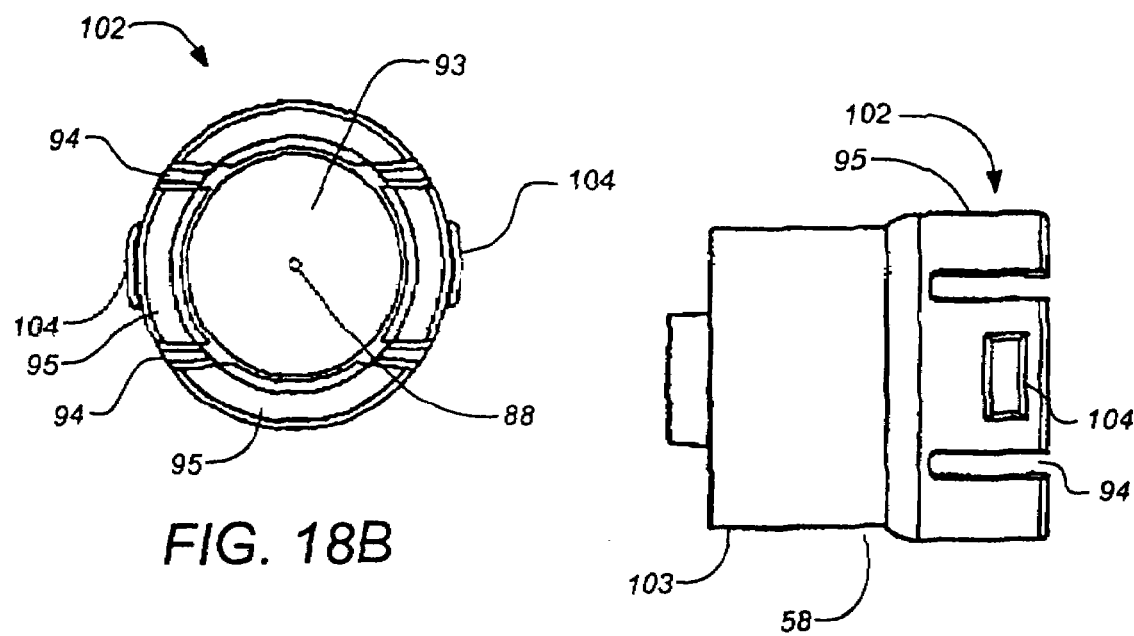
FIG. 18B
FIG. 18C

RESERVOIR CONNECTOR

CROSS-REFERENCE TO RELATED APPLICATIONS

This application is a continuation application of U.S. patent application Ser. No. 09/974,312, filed Oct. 10, 2001, and entitled "RESERVOIR CONNECTOR" which in turn claims priority under 35 U.S.C. §120 from U.S. patent application Ser. No. 09/428,818, filed Oct. 28, 1999, now U.S. Pat. No. 6,585,695, issued Jul. 1, 2003, and entitled "RESERVOIR CONNECTOR" which in turn claims priority from U.S. Provisional Patent Application No. 60/106,237, filed on Oct. 29, 1998, the contents of all of which are incorporated herein by reference.

BACKGROUND OF THE INVENTION

1. Field of the Invention

This invention relates generally to improvements in syringe or reservoir interfaces for use in infusion pumps such as those used for controlled delivery of medication to a patient. More specifically, this invention relates to an improved connection interface between a reservoir or syringe and infusion set tubing or a standard luer connector.

2. Description of the Related Art

Infusion pump devices and systems are relatively well-known in the medical arts, for use in delivering or dispensing a prescribed medication such as insulin to a patient. In one form, such devices comprise a relatively compact pump housing adapted to receive a syringe or reservoir carrying a prescribed medication for administration to the patient through infusion tubing and an associated catheter.

The infusion pump includes a small drive motor connected via a lead screw assembly for motor-driven advancement of a reservoir piston to administer the medication to the user. Programmable controls are normally provided for operating the drive motor continuously or at periodic intervals to obtain a closely controlled and accurate delivery of the medication over an extended period of time. Such infusion pumps are utilized to administer insulin and other medications, with exemplary pump constructions being shown and described in U.S. Pat. Nos. 4,562,751; 4,678,408; 4,685,903; 5,080,653 and 5,097,122, which are all incorporated by reference herein.

Infusion pumps of the general type described above have provided significant advantages and benefits with respect to accurate delivery of medication or other fluids over an extended period of time. The infusion pump can be designed to be relatively compact as well as water resistant, and may thus be adapted to be carried by the user, for example, by means of a belt clip. As a result, important medication can be delivered to the user with precision and in an automated manner, without significant restriction on the user's mobility or life-style, including the ability to participate in water sports.

Infusion sets refer to the tubing and connection apparatus which provide a path for the medication to flow to the user from the reservoir or syringe located in the pump. The connectors for attaching the infusion set tubing to the reservoirs can take various forms. A luer connection is a commonly used connection method. Nevertheless, it remains desirable to develop improved designs of connection methods to facilitate infusion procedures and to provide suitable interface connections which are water resistant so as to permit a user to participate in water sports.

SUMMARY OF THE INVENTION

The invention disclosed herein has a number of embodiments. A typical embodiment of the invention is an apparatus for connecting a reservoir having a septum and a base to a conduit, such as infusion set tubing. In certain aspects of the present invention, the apparatus comprises a cap and a releasable coupler which is adapted to releasably couple the base to the cap in one of two positions. A piercing member, such as a needle, is coupled to the conduit. The needle is disposed in the cap in a position other than the interior of the reservoir when the base is in the first position. The needle is further disposed to pierce the reservoir septum when the base is in the second position.

In another embodiment, the apparatus is used for connecting a reservoir having a septum and a base to a housing as well as to a conduit. The housing has a housing engagement member, such as a thread. The apparatus comprises a cap and a releasable coupler which is adapted to releasably couple the base to the cap in one of two positions. A piercing member, such as a needle, is releasably coupled to the conduit. The needle is disposed in the cap in a position other than the interior of the reservoir when the base is in the first position. The needle is further disposed to pierce the reservoir septum when the base is in the second position. The cap further includes an engagement member, such as a thread, which is adapted to engage with the housing engagement member.

In another embodiment, the cap further includes a vent port which is covered with hydrophobic material. This permits air to pass through the cap while preventing water from doing so.

In another embodiment, an integral apparatus is used for connecting a reservoir having a septum and an annular shoulder and a conduit. This embodiment includes a conduit portion, a piercing member coupled to the conduit and adapted to pierce the septum and a reservoir connector portion coupled to the conduit portion and comprising an open-ended cylindrical member. The open-ended cylindrical member is releasably coupleable to the reservoir and the piercing member pierces the septum when so coupled. Typically, the conduit is a luer connector.

BRIEF DESCRIPTION OF THE DRAWINGS

Referring now to the drawings in which like reference numbers represent corresponding parts throughout:

FIGS. 16A-16C are views of an integral medication reservoir connection embodiment;

FIGS. 18A-18C are views of an another embodiment of an integral medication reservoir connection embodiment without a neck portion.

DETAILED DESCRIPTION OF THE PREFERRED EMBODIMENT

Figure 1:
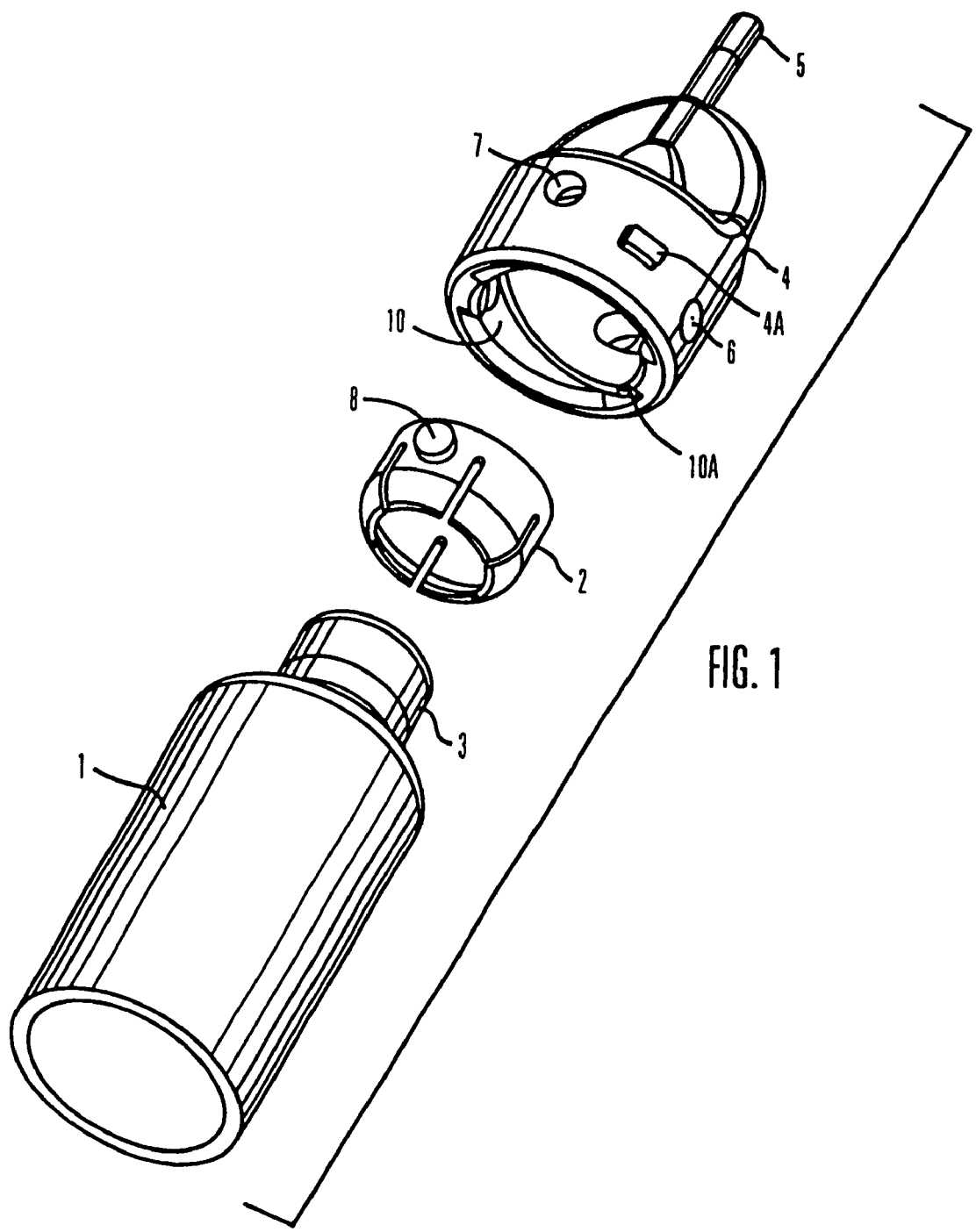
FIG. 1 is an exploded, perspective view of a medication reservoir connection interface apparatus.

In the following description, reference is made to the accompanying drawings which form a part hereof and which illustrate several embodiments of the present invention. It is understood that other embodiments may be utilized and structural and operational changes may be made without departing from the scope of the present invention.

As shown in the drawings for purposes of illustration, the invention is embodied in an interface for connecting a syringe or a medication reservoir to a conduit, such as infusion set tubing or an external needle, as well as to an infusion pump. In one embodiment, a base is provided which is adapted to receive a reservoir. A cap is provided which is adapted to be releasably coupled to the base in one of two positions. The releasable coupler comprises a pair of detents projecting from the base and two pairs of detent openings in the cap which are adapted to removably engage the base detents.

A piercing member, such as a needle, is disposed in the interior of the cap in such a manner that the needle is separated from the reservoir septum when the base detents are in the first pair of cap detent openings, and the needle pierces the reservoir septum when the base detents are in the second pair of cap detent openings. When the reservoir, the base and the cap are connected, an integrated unit is formed which is then capable of being inserted in the infusion pump housing. Engagement members, such as threads, for the cap and the pump housing are used to secure the integrated unit in the housing.

In another embodiment, an integral apparatus is used for connecting a reservoir having a septum and an annular shoulder and a conduit. The apparatus comprises a conduit portion, a piercing member coupled to the conduit and adapted to pierce the septum and a reservoir connector portion coupled to the conduit portion and comprising an open-ended cylindrical member. The open-ended cylindrical member is releasably coupleable to the reservoir and the piercing member pierces the septum when so coupled. Typically, the conduit is a luer connector.

Figure 2:
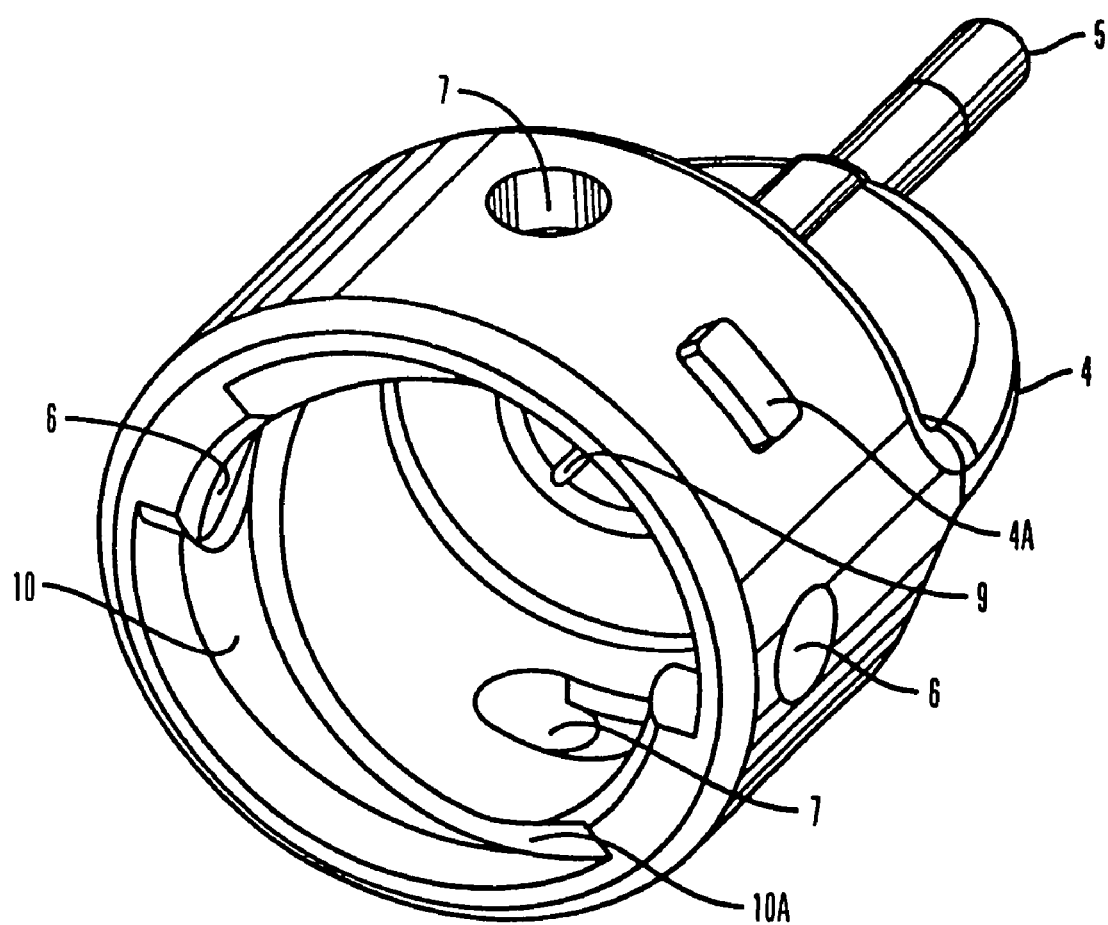
FIG. 2 is a perspective view of a cap used as a medication reservoir connection interface apparatus.

FIGS. 1 and 2 show an infusion set connector interface for attachment to a medication reservoir. The connector interface is comprised of a base 2 and a cap 4. The cap 4 includes a needle 9 located internal to the cap housing. FIG. 1 is an exploded view, and therefore, the base 2 would normally be fixedly attached to a reservoir 1 by securing it around the swage 3, which holds the reservoir septum. However, alternative embodiments of the present invention include a removable base so that the connector interface could be used with standard reservoirs, cartridges or syringes which were not initially manufactured with the base attached.

The cap 4 portion of the connector interface is removably attached to the base 2 with a releasable coupler. In one embodiment, the releasable coupler is comprised of detents formed on the base 2 and detent openings disposed in the cap 4. Two detents 8 are disposed on the sides of the base 2 and are spaced 180° radially apart. Only one detent 8 is shown in FIG. 1. The detents 8 are sized to fit in the two lower detent openings 6, or alternatively, in the two upper detent openings 7 which are formed in the cap 4. As with the pair of detents 8, each of the lower detent openings 6 and each of the upper detent openings 7, respectively, are radially spaced apart by 180°.

In operation, the base 2 and the reservoir 1 form an integrated unit which in turn is to be connected to the cap 4. In connecting this integrated base/reservoir unit to the cap 4, the base 2 is inserted into the lower end of the cap 4 until the detents 8 snap into the lower detent openings 6. This is accomplished by moving the detents 8 over internal cam surfaces 10 toward the lower detent openings 6. The cam surfaces act as ramps which compress the detents 8 sufficiently to permit them to snap into the lower detent openings 6. Internal threads 10a guide the detents 8 into position.

When the base/reservoir unit is in this first, lower position, the needle 9 is positioned apart from the septum (not shown) of the reservoir 1. Thus the needle does not pierce the septum while the base/reservoir unit is in this first position. When the base/reservoir unit is connected to the cap in this fashion, an integrated cap/base/reservoir unit is thereby formed. Conveniently, such an integrated cap/base/reservoir unit can be sold or stored for long periods of time in this fashion. Alternatively the end user can assemble this unit shortly prior to placing it in the pump for use.

When the user desires to insert the cap/base/reservoir unit in the pump housing and commence dispensing the medication through a conduit, such as insertion set tubing 5, the base 2 is moved to the second position within the cap 4. This is accomplished by twisting the base/reservoir unit while pushing it further into the cap 4. The detents 8 disengage from the lower detent openings 6 and engage into the upper detent openings 7. Additional internal threads 10a of the cap 4 serve to guide the detents 8 over additional cam surfaces 10 from their first position in the lower detent openings 6 to the second position in the upper detent openings 7.

In one embodiment, the threads and the spacing between the lower detents 6 and the upper detents 7 is such that a one quarter (¼) turn of the base will cause the base/reservoir unit to travel from the first to the second position. The needle 9 is disposed so that when the base/reservoir unit is in the second position, the needle pierces the septum of the reservoir 1. Thus the movement of the base/reservoir unit from the first to the second position within the cap serves to cause the needle to pierce the reservoir's septum, thus permitting the fluid in the reservoir to flow into the needle 9 and the insertion set tubing 5.

After this connection is made, the reservoir, base and cap form a unit which can be releasably secured in the housing of a medication infusion pump (not shown). Detents 4a extend radially from the exterior of the cap and are adapted to engage into detent openings (not shown) in the pump housing. In an alternative embodiment, the cap 4 can include external threads (not shown) which are used to engage the threads of the pump housing in order to secure the reservoir/base/cap unit into the housing.

Figure 3:
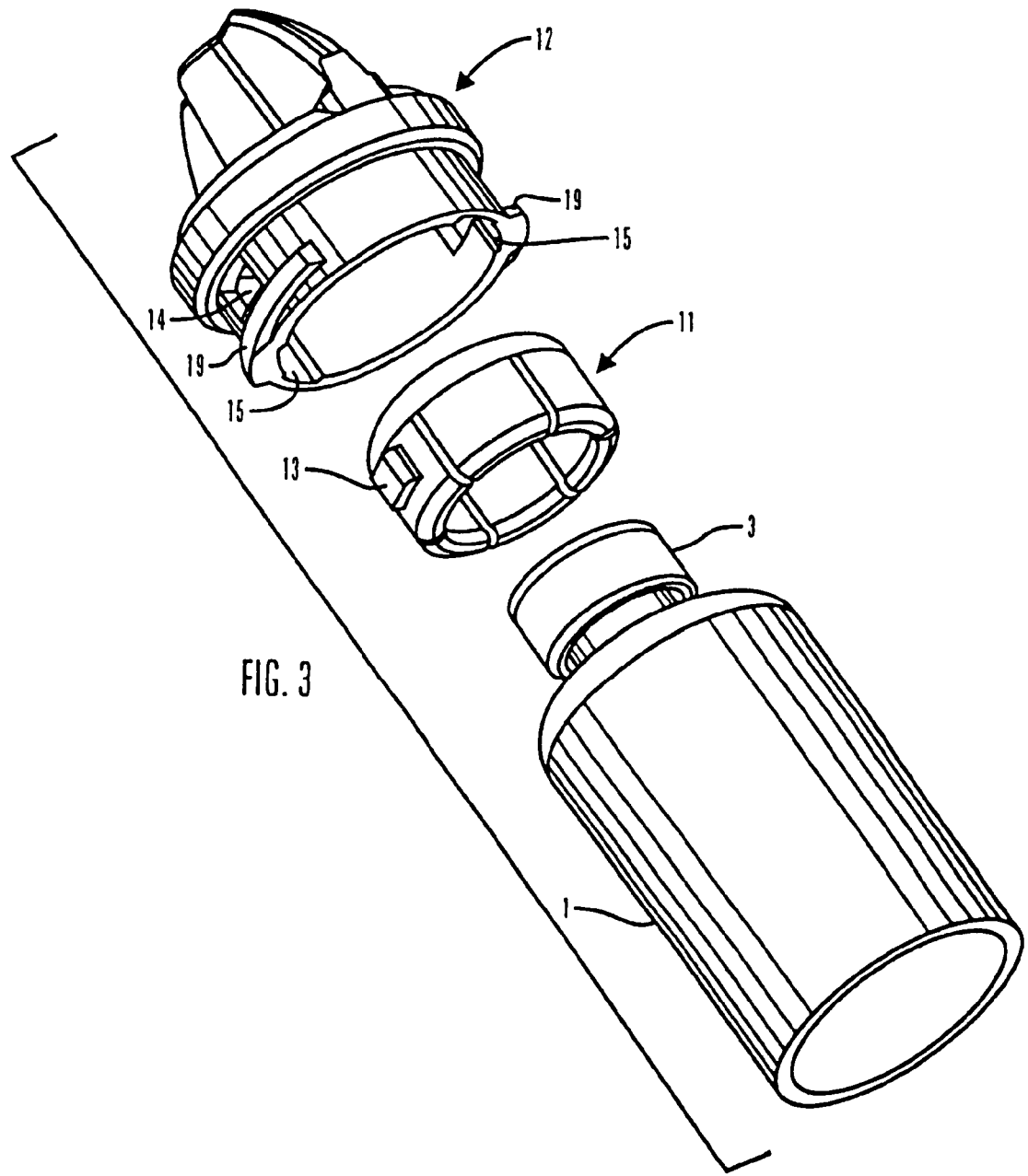
FIG. 3 is an exploded, perspective view of an alternative embodiment of a medication reservoir connection interface apparatus.
Figure 4:
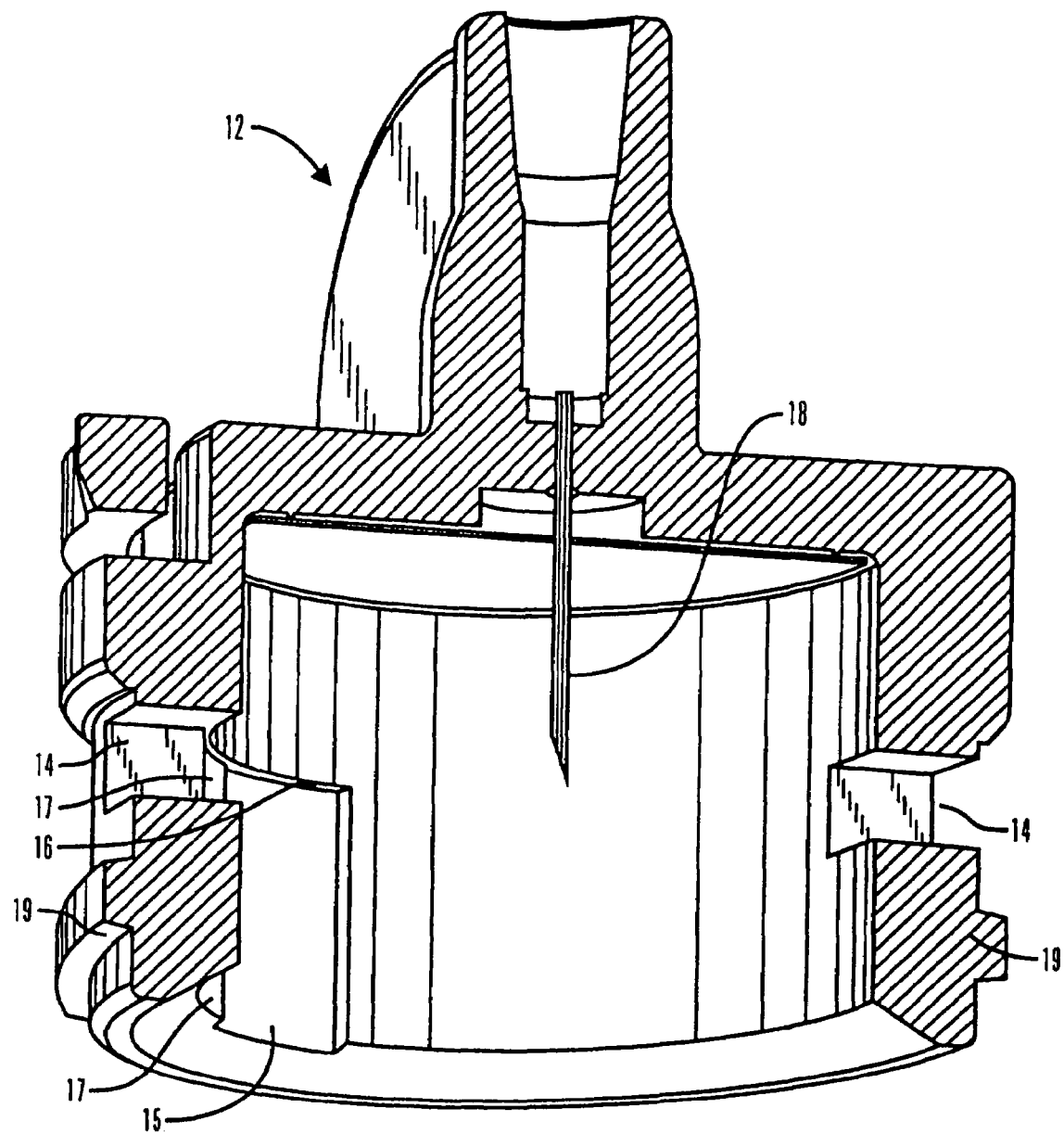
FIG. 4 is a side, cut-away view of a cap used as a medication reservoir connection interface apparatus.

FIGS. 3 and 4 show an alternative embodiment of the infusion set connector interface. The connector interface is comprised of a base 11 and a cap 12. The cap 12 includes a needle 18 located internal to the cap housing (FIG. 4). The base 11 would normally be fixedly attached to the reservoir 1 by securing it around the swage 3. However, alternative embodiments of the present invention include a removable base so that the connector interface could be used with standard reservoirs, cartridges or syringes which were not initially manufactured with the base attached.

The cap 12 portion of the connector interface is removably attached to the base 11 with a releasable coupler. In this embodiment, the releasable coupler is comprised of detents 15 formed on the base 11 and detent openings disposed in the cap 12. Two detents 13 are disposed on the sides of the base 11 and are spaced 180° radially apart. Only one detent 13 is shown in FIG. 3. The detents 13 are sized to fit in two detent openings 14 which are formed in the cap 12. As with the pair of detents 13, each of the detent openings 14 are radially spaced apart by 180°.

In operation, the base 11 and the reservoir 1 form an integrated unit which in turn is to be connected to the cap 12. In connecting this integrated base/reservoir unit to the cap 12, the base 11 is inserted into the lower end of the cap 12. The detents 13 slide into matingly shaped and longitudinally open entry slots 15 formed within the interior walls of the cap 12. When the base 11 is fully inserted in the cap 12, the leading edges of the detents 13 abut an annular stop shoulder 16 formed within the cap 12. After the detents 13 are in this position, the base 11 is rotated within the cap 12 toward a locked position. Referring to FIG. 4, this rotation displaces the detents 13 in a rotational direction for engagement with cam surfaces 17 formed within the cap 12. The rotational force on the detents 13 over the cam surfaces 17 provides a compression force on the detents 13. Continued rotation of the base 11 displaces the detents 13 past the cam surfaces 17 and into alignment with the detent openings 14. The detents 13 enter the detent openings 14 with a snap-action. Thus, the detents 13 are effectively locked within the detent openings 14 to prevent longitudinal separation of the base 11 from the cap 12.

In the preferred embodiment, the internal needle 18 of the cap 12 is disposed so that when the base/reservoir unit is fully inserted in the cap 12, the needle pierces the septum (not shown) of the reservoir 1. Thus the insertion force of the base/reservoir unit to the point where the detents 13 abut the annular stop shoulder 16 causes the needle 18 to pierce the septum, thus permitting the fluid in the reservoir to flow into the needle 18 and the insertion set tubing (not shown).

After this connection is made, the reservoir, base and cap form a unit which can be releasably secured in the housing of a medication infusion pump. (not shown) The cap 12 includes external threads 19 which are used to engage the threads of the pump housing in order to secure the reservoir/base/cap unit into the housing. In the preferred embodiment, the threads 19 have an eight threads per inch ("TPI"), 2 start profile. Moreover, they have a square shaped cross section which maximizes their holding strength. Other thread profiles and cross-sections may be used however.

When disconnection of the base 11 from the cap 12 is desired, the base 11 must be reverse-rotated within the cap 12, to move the detents 13 past the cam surfaces 17 into re-alignment with the entry slots 15. Such reverse-rotation of the coupler can be performed relatively easily, but essentially requires an affirmative intent by the user to disconnect the coupling. When the detents 13 are re-aligned with the entry slots 15, the cap 12 and base 11 can be separated easily with minimal longitudinal force.

Figure 5:
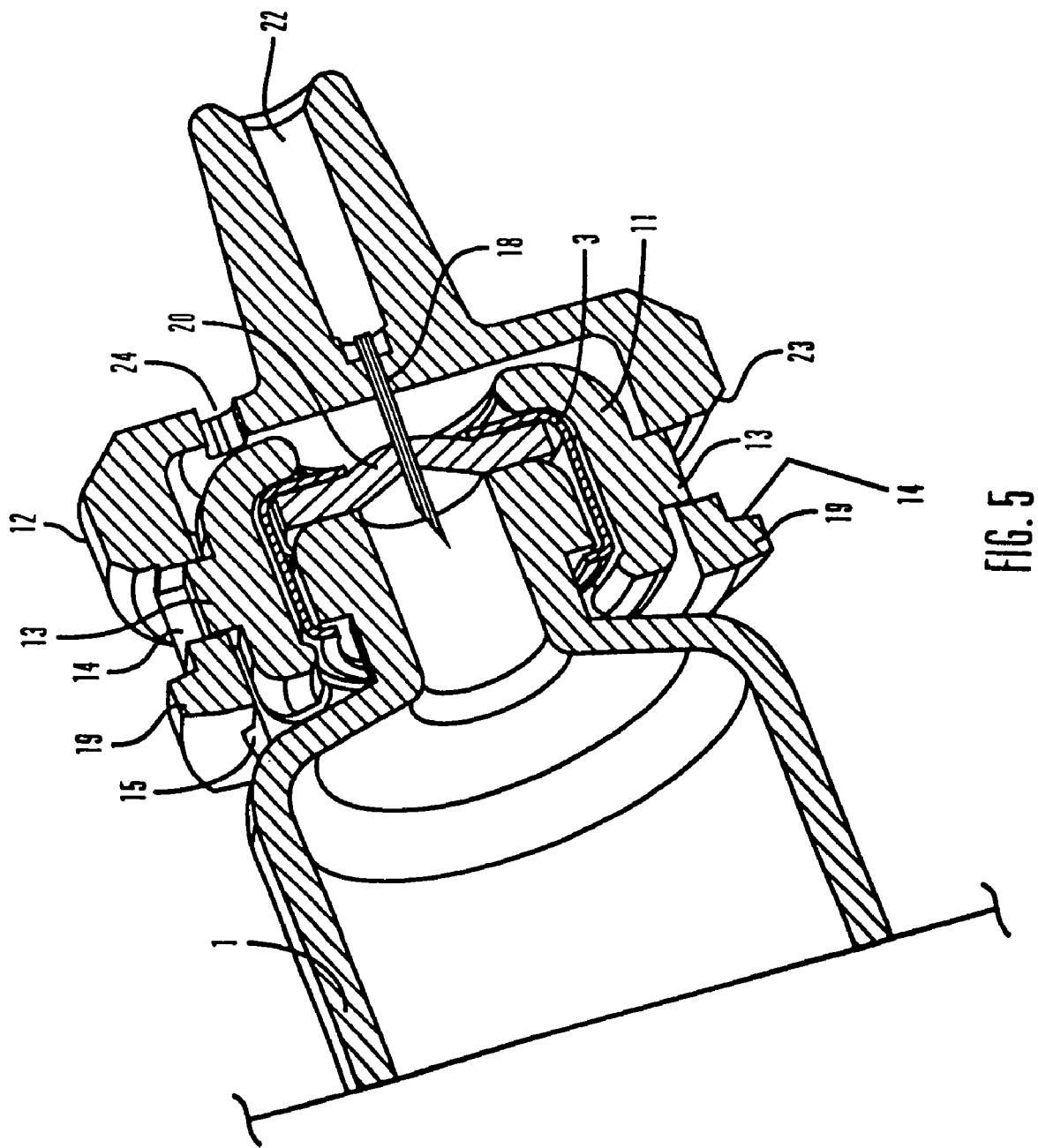
FIG. 5 is a side, plan cut-away view of a medication reservoir connection interface apparatus with a needle inserted into a reservoir.

FIG. 5 shows a cross sectional view of the reservoir/base/cap integrated unit in accordance with the embodiment of FIGS. 3 and 4. The reservoir 1 includes a crimp seal swage 3 which encloses the outer periphery of the rubber septum 20 in order to secure the septum 20 to the reservoir 1 and form a water tight seal. With the base 11 in the locked position as shown, the detents 13 of the base 11 are locked into the detent openings 14 to securely attach the base/reservoir unit into the cap 12. The needle 18 pierces the rubber septum 20, thus permitting the flow of liquid through the needle 18 and into the infusion set tubing cavity 22. Infusion set tubing (not shown) is secured into the cavity 22 to allow the liquid to continue its flow to the user.

In the preferred embodiment, the conduit from the cap 12 is infusion set tubing. However in an alternative embodiment, the conduit comprises a second needle (not shown). This is secured into the cavity 22 with the point of the second needle extending outward. With this arrangement, the connector serves as an apparatus for permitting the refilling of the reservoir 1. The second, external needle would pierce the septum of a supply vial of fluid. The fluid could then be drawn into the cap in a reverse flow and into the reservoir 1 via the internal needle 18.

In the embodiment shown in FIG. 5, infusion set tubing is secured to the cavity 22 to allow liquid to flow to the user. The cavity 22 is disposed in the raised portion of the cap 12. In an alternative embodiment, however, the raised portion of the cap 12 can be in the shape of a standard luer fitting 47 shown in FIG. 13.

Referring to FIG. 5, in one embodiment the base 11 is formed around and fixedly attached to the crimp seal swage 3 portion of the reservoir 1. In an alternative embodiment, however, the base 11 is not fixedly attached to the reservoir. Rather, the base 11 is a separate unit which is adapted to be releasably secured to the reservoir via a friction fit. This arrangement permits the connector apparatus to be used with standard reservoirs.

Still referring to FIG. 5, the cap 12 includes threads 19 for securing the assembly into the pump housing (not shown). A shoulder 23 is formed as part of the cap 12 and is adapted to seat against the pump housing to form a water tight seal. This prevents any water which is exterior to the housing from entering, thus permitting the user to engage in water sports.

The construction of these pumps to be water resistant can give rise to operational problems. As the user engages in activities which expose the pump to varying atmospheric pressures, such as for example, swimming or traveling in an airplane, differential pressures can arise between the interior of the air tight/water-resistant housing and the atmosphere. Should the pressure in the housing exceed external atmospheric pressure, the resulting forces could cause the reservoir piston to be driven inward thus delivering unwanted medication. Alternatively, should the pressure in the housing be less than the external pressure, the resulting forces could cause the infusion pump motor to work harder to advance the reservoir piston.

To address this problem, a preferred embodiment of the invention includes a vent which permits water resistant housing construction. The cap 12 includes a plurality of vent ports 24, only one of which is shown in FIG. 5. The vent ports 24 permit equalization of pump housing pressure to atmospheric pressure. Hydrophobic material (not shown) covers the interior openings of the vent ports 24. Hydrophobic material permits air to pass through the material while preventing water or other liquids from doing so, thus permitting water resistant venting. The preferred embodiment uses a hydrophobic material such as Gore-Tex®, PTFE, HDPE, or UHMW polymers from sources such as W.I. Gore & Associates, Flagstaff, Ariz., Porex Technologies, Fairburn, Ga., DeWAL Industries, Saunderstown, R.I., or Pall Specialty Materials, Port Washington, N.Y.

Figure 14A:
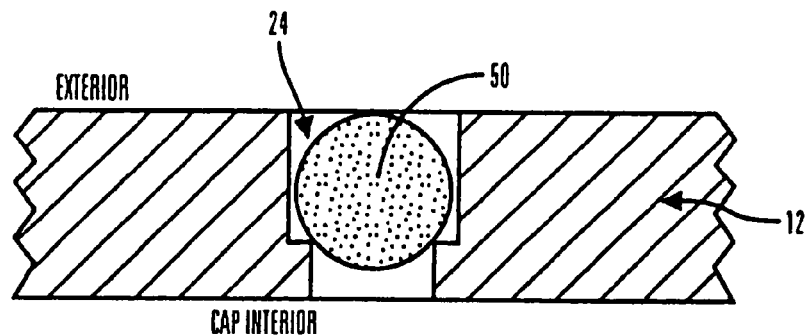
FIGS. 14A-14C are cross-sectional views of various embodiments of venting ports for use with a reservoir connection interface apparatus or adapter.
Figure 14B:
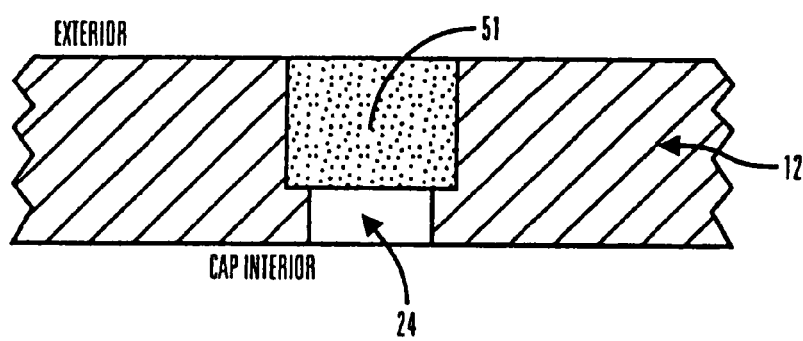
Figure 14C:
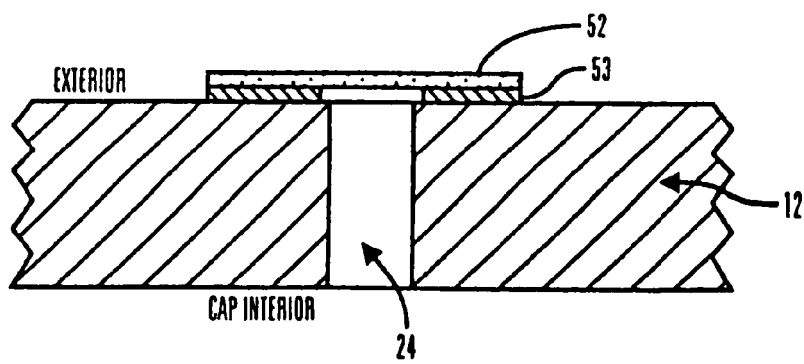

These materials are available in sheet form or molded (press and sintered) in a geometry of choice. Referring to FIGS. 14A-14C, preferred methods to attach this material to the cap 12 include molding the hydrophobic material into a sphere 50 (FIG. 14A) or a cylinder 51 (FIG. 14B) and pressing it into a cavity in the pre-molded plastic housing. Alternatively, a label 52 (FIG. 14C) of this material could be made with either a transfer adhesive or heat bond material 53 so that the label could be applied over the vent port 24. Alternatively, the label could be sonically welded to the housing. In either method, air will be able to pass freely, but water will not.

In an alternative embodiment which is not shown, the venting is accomplished through a vent port located in the pump housing. This is described in greater detail in copending U.S. patent application Ser. No. 09/429,352, filed Oct. 28, 1999, which application is incorporated by reference in its entirety. Alternatively, vent ports can be placed both in the cap 12 as well as the pump housing.

An advantage of placing the vent port and hydrophobic material in the cap 12, as opposed to in the pump housing only, is that the infusion set and its related connectors are disposable and are replaced frequently with each new reservoir or vial of medication. Thus, new hydrophobic material is frequently placed into service. This provides enhanced ventilation as compared with the placement of hydrophobic material in only the pump housing. Material in this location will not be replaced as often and thus is subject to dirt or oil build up which will retard ventilation.

As an alternative to the use of hydrophobic material, water can be prevented from flowing through the vent port by other apparatuses, such as the use of relief valves.

Figure 6:
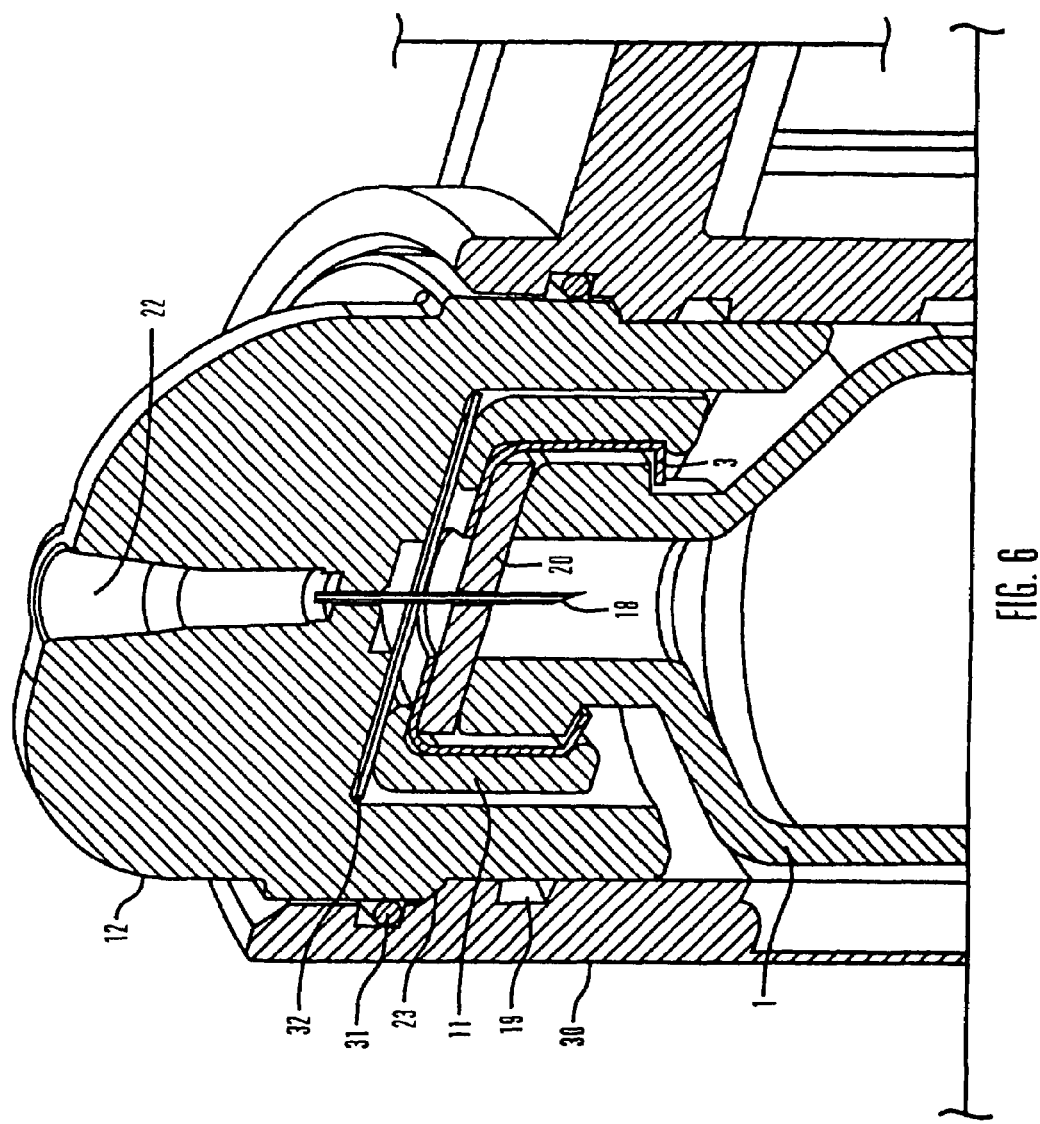
FIG. 6 is a side, plan cut-away view of a medication reservoir connection interface apparatus which is inserted into a pump housing.

FIG. 6 shows a cross-sectional view of the reservoir/base/cap unit in accordance with the embodiment of FIGS. 3 and 4 which is secured into a pump housing 30. The threads 19 of the cap 12 engage the pump housing threads. Rather than the use of threads, an alternative embodiment (not shown) of the cap 12 could include detents extending radially from the exterior of the cap 12 which are adapted to engage detent openings in the pump housing.

The shoulder 23 portion of the cap 12 seats against the pump housing 30 to permit water tight construction. Further aiding in the watertight construction is an O-ring seal 31 which is disposed in the pump housing 30 and located just above the shoulder 23. In the preferred embodiment, the vent material 32 is comprised of hydrophobic material and is sonic welded to the upper interior surface of the cap 12. Alternatively, the vent material 32 could be attached to the cap 12 with an adhesive. The vent ports are not shown in FIG. 6.

Although the foregoing description of the venting was in connection with the embodiment of FIGS. 3-6, this feature is also applicable to the embodiment of FIGS. 1-2.

Figure 7:
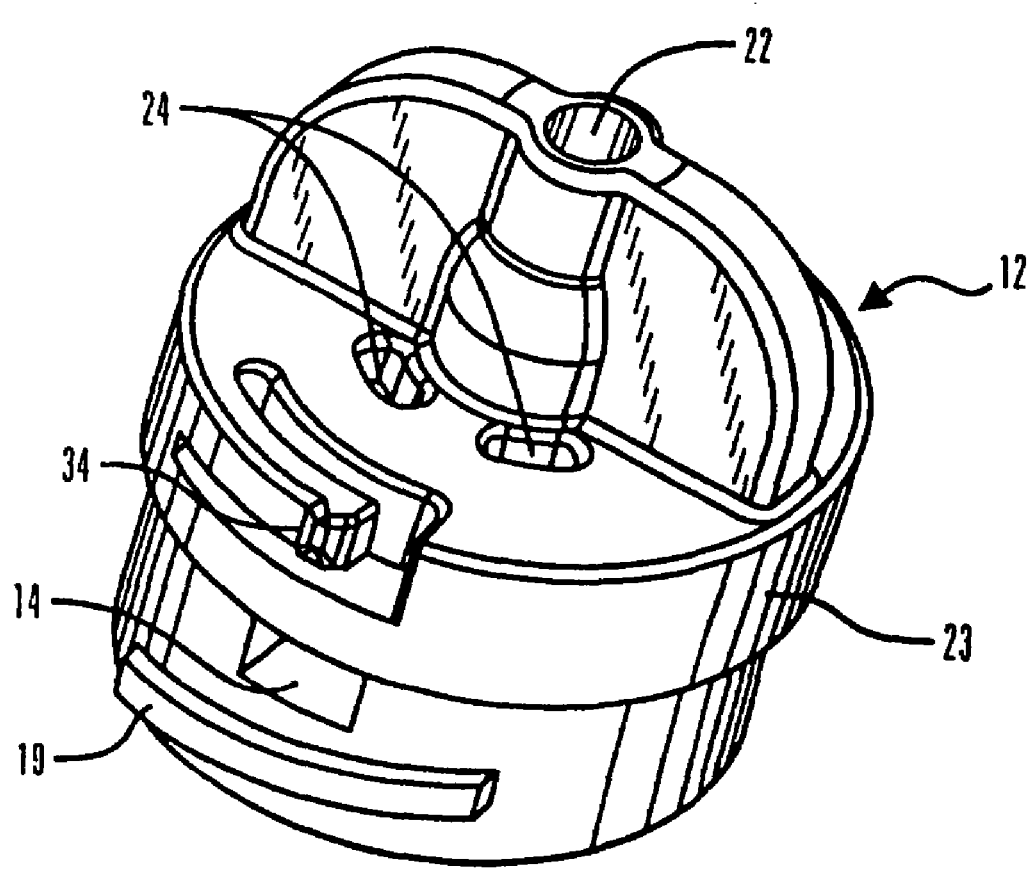
FIG. 7 is a perspective view of an alternative embodiment of a medication reservoir connection interface apparatus.
Figure 8:
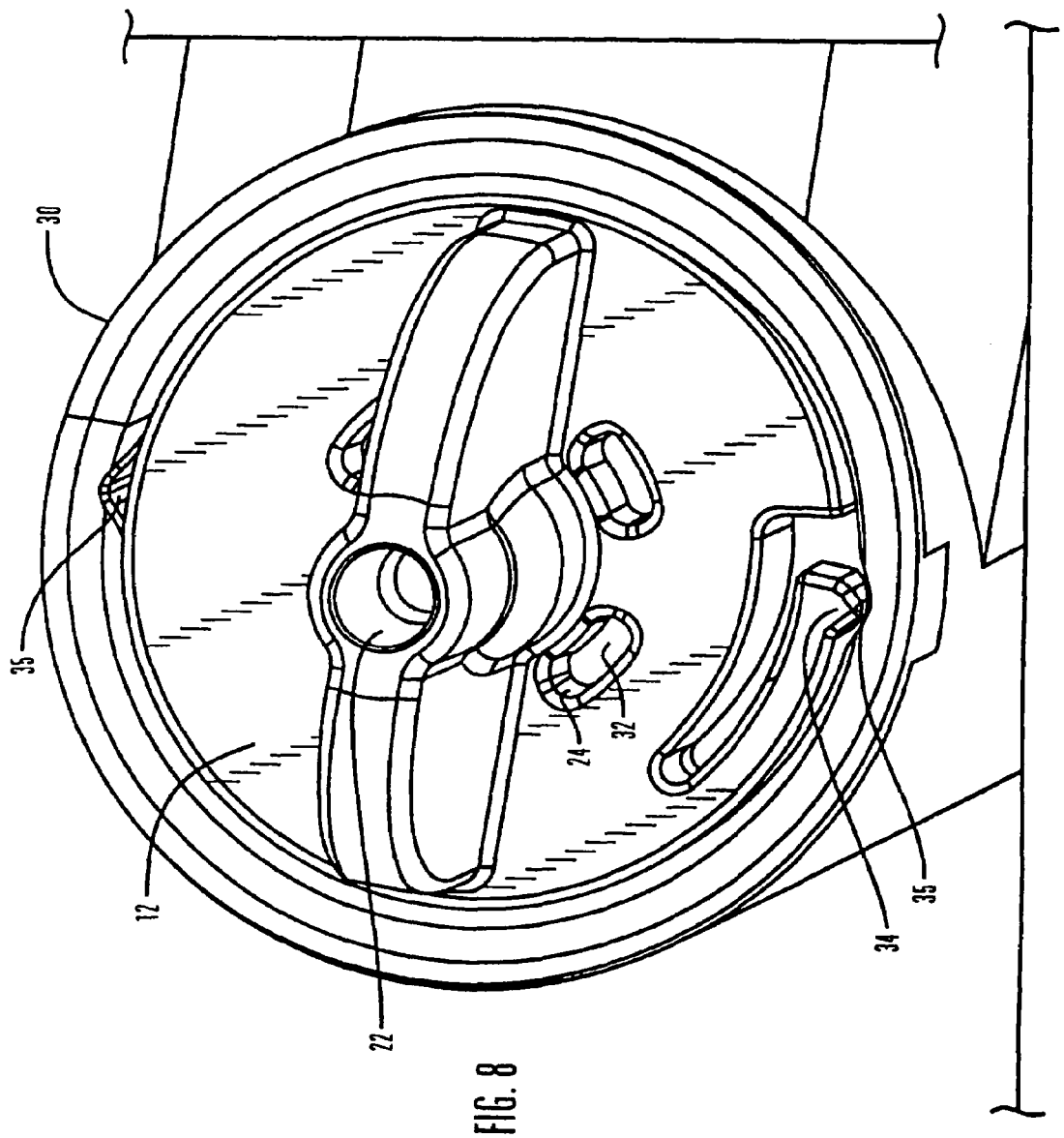
FIG. 8 is a perspective top view of an alternative embodiment of a medication reservoir connection interface apparatus which is secured into a pump housing.

FIGS. 7 and 8 show an alternative embodiment of the cap 12. Referring to FIG. 7, a cap engagement member consists of a detent arm 34 which is formed in the upper portion of the cap 12. The purpose of the detent arm 34 is to securely engage the cap 12 into the pump housing. FIG. 8 shows a top view of the cap 12 positioned in the pump housing 30. The pump housing 30 has two case lock recesses 35 disposed in the circular rim of the housing. The detent arm 34 snaps into either of the case lock recesses 35. This engagement results in a "click" when the cap 12 is appropriately seated, thus providing both tactile and audible feedback to the user that the cap is securely engaged in the pump housing. Moreover, the detent arm 34 aligning with the recess 35 also serves as a visual indicator that the cap 12 is appropriately seated.

Figure 9:
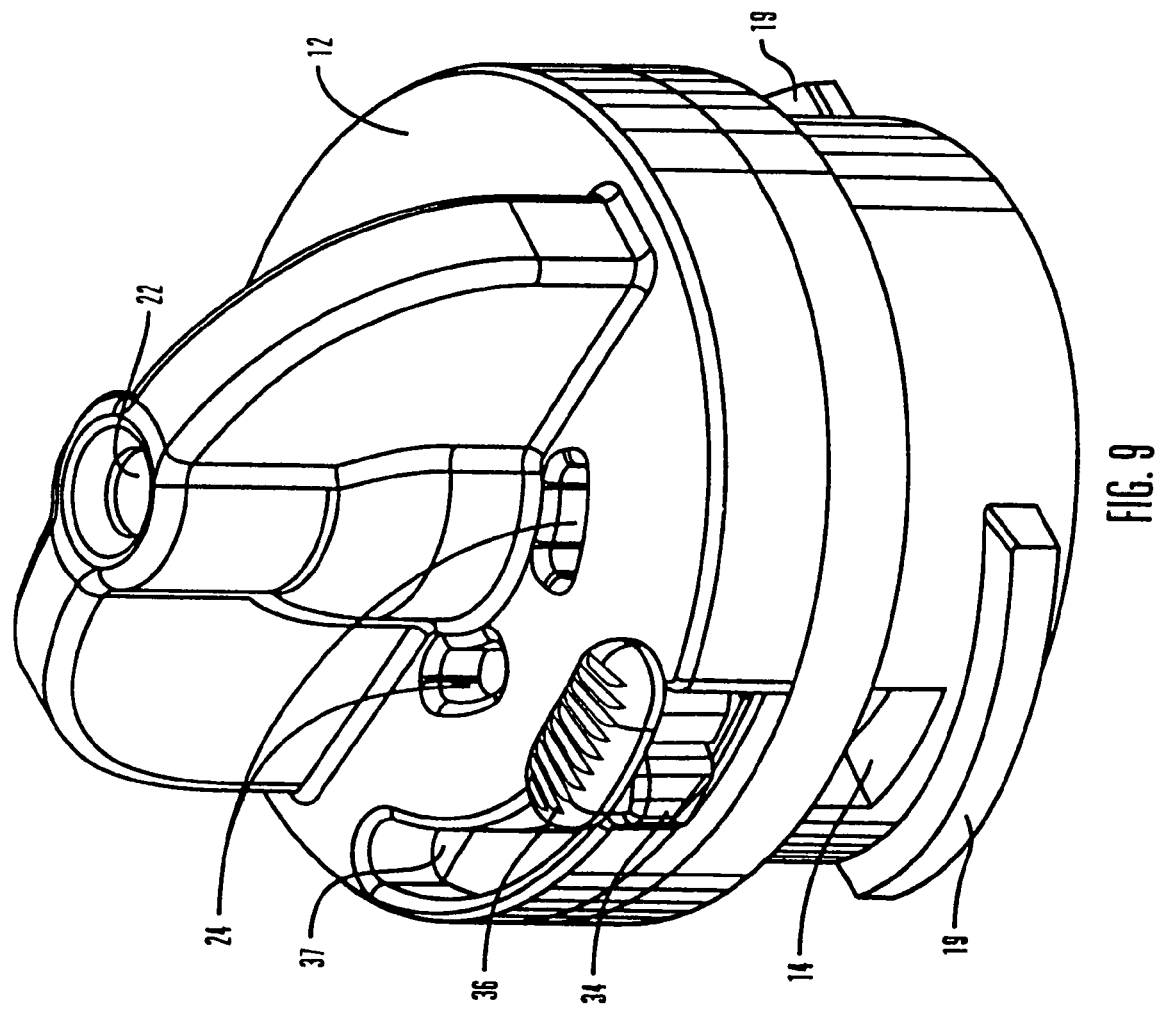
FIG. 9 is a perspective view of an alternative embodiment of a medication reservoir connection interface apparatus.

FIG. 9 shows an alternative embodiment of the cap 12 which contains a child safety feature. The cap 12 includes a locking member which consists of a safety tab 36 disposed in a groove 37. The safety tab 36 is sized such that it is able to slide along the length of the groove 37. When the safety tab 36 is in the position shown in FIG. 9, the detent arm 34 is unable to retract from its engaged position. Thus when the cap 12 is seated into the pump housing 30 (not shown) and the detent arm is seated into the case lock recess 35 (not shown), the safety tab 36 will prevent the detent arm 34 from disengaging from the case lock recess 35 thus more securely locking the cap 12 in the pump housing.

Thus for example, a parent could slide the safety tab 36 from the unlocked location in the groove 37 to the locked location shown in FIG. 9 so that it would be more difficult for a young child or infant to inadvertently remove the cap/base/reservoir unit from the pump housing. On the other hand, when the safety tab 36 is moved to the opposite end of the groove 37, the detent arm 34 is able to retract thus permitting removal of the cap 12 from the pump housing.

Although the foregoing description of the cap engagement member and child safety tab was in connection with the embodiment of FIGS. 3-9, this feature is also applicable to the embodiment of FIGS. 1-2.

Figure 10:
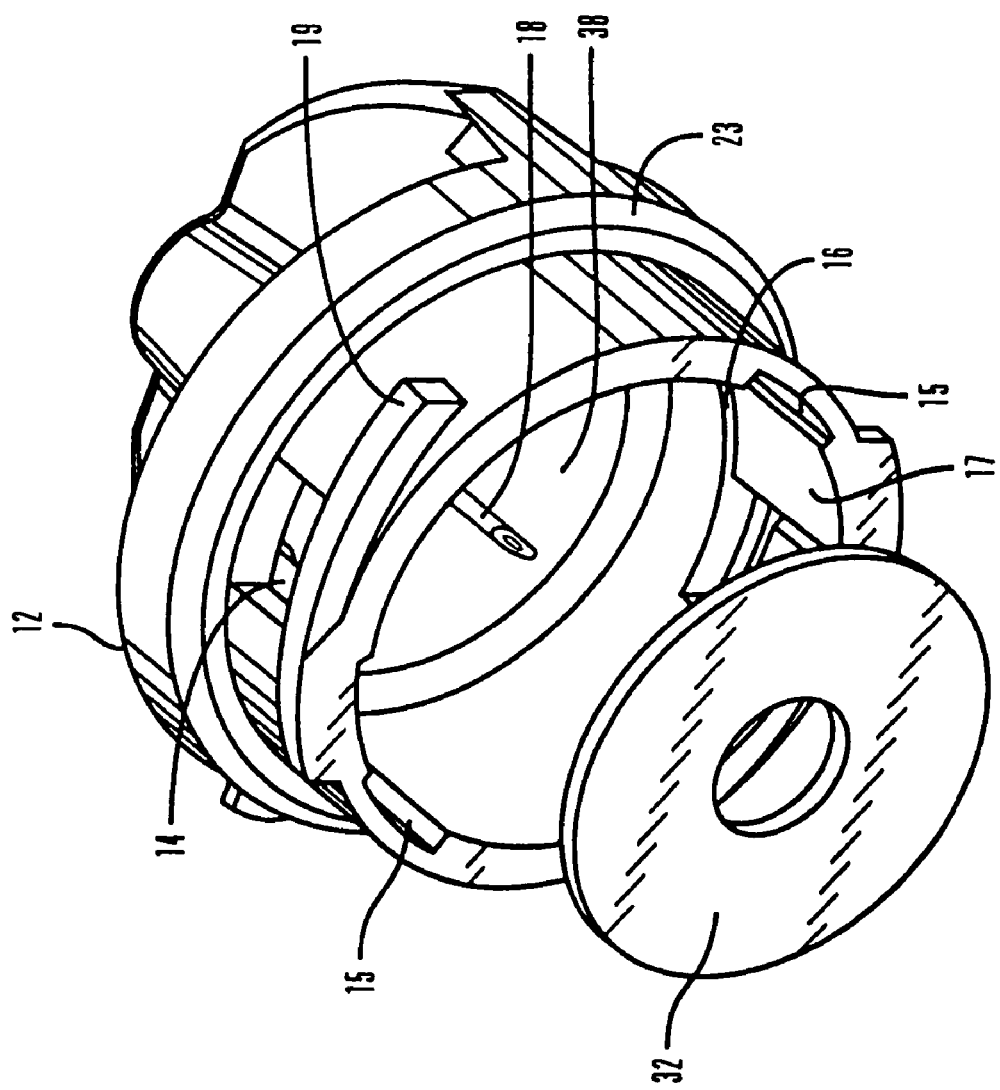
FIG. 10 is an exploded, perspective view of a cap used as a medication reservoir connection interface apparatus.

FIG. 10 shows an exploded view of the cap 12 and the vent material 32. In the preferred embodiment, the vent material is made of hydrophobic material and is formed in a circular shape with a circular hole in the center. The vent material 32 is attached to the upper interior surface 38 of the cap 12 via sonic welding or an adhesive. When it is so attached, the needle 18 protrudes through the center hole of the vent material 32 but the interior openings of the vent ports 24 (not shown) are covered.

Figure 11:
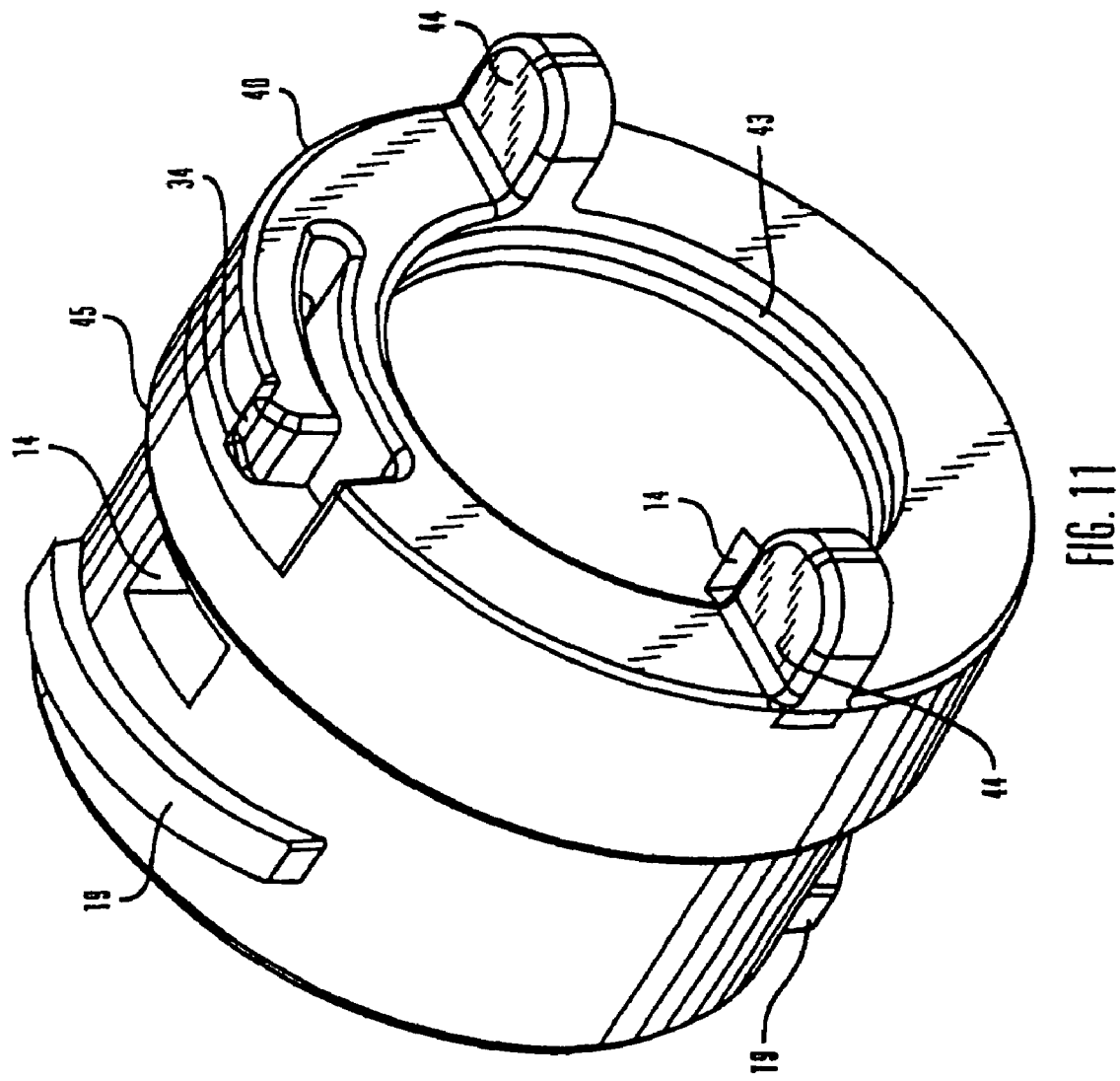
FIG. 11 is a perspective view of a medication reservoir connection interface adapter.
Figure 12:
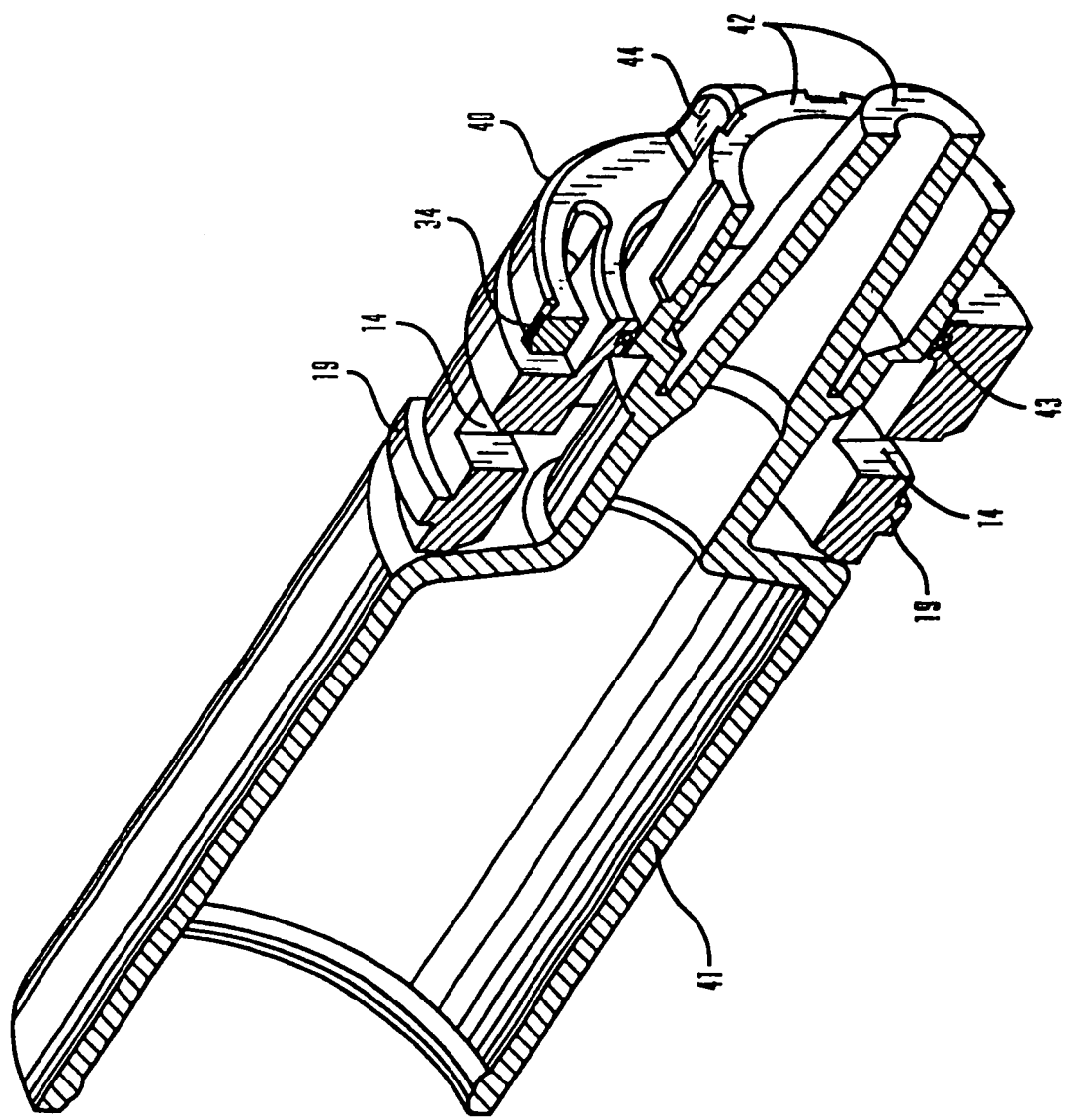
FIG. 12 is a cross-sectional view of a medication reservoir connection interface adapter.

FIGS. 11 and 12 show an embodiment of the present invention where an adapter 40 is provided to allow a standard style syringe 41 with an integrated luer fitting 42 to be mounted and sealed in the pump housing. The syringe 41 is inserted through the center of the adapter 40 and held into place by a friction fit. The O-ring seal 43 in the adapter 40 seats against the syringe wall in order to prevent water and dirt from entering the pump housing.

A shoulder 45 is formed as part of the adapter 40 and is adapted to seat against the interior of the pump housing to form a water tight seal. Two tabs 44 are formed on the top surface of the adapter 40 and provide a surface for the user to grip the adapter 40 and twist it so that the adapter threads 19 engage the threads (not shown) of the pump housing. A detent arm 34 is formed in the upper portion of the adapter 40. Its purpose is to securely lock the adapter 40 into the pump housing (not shown) in the same manner as is shown in FIG. 8. Although not shown in FIGS. 11 and 12, the adapter 40 can further contain vent ports covered with hydrophobic material or a relief valve in order to permit water resistant venting of the pump housing in the same manner as previously described with other embodiments.

Figure 13:
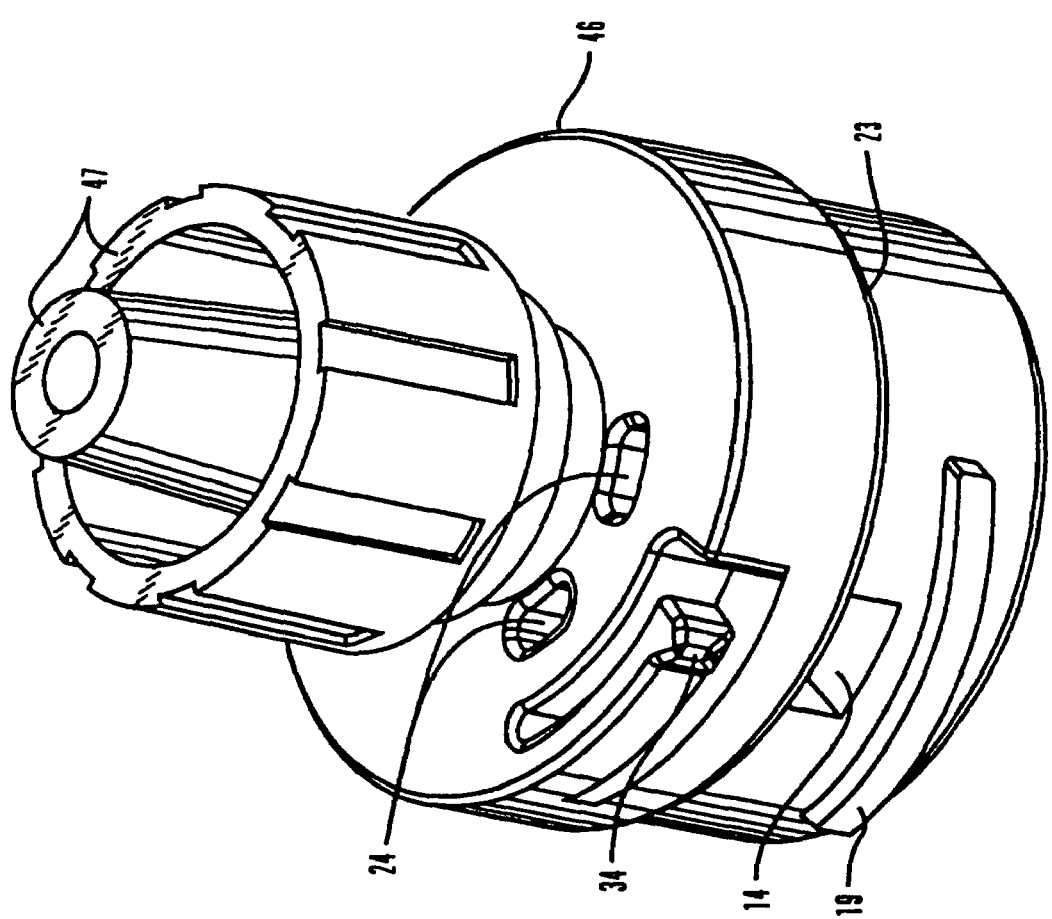
FIG. 13 is a perspective view of an alternative embodiment of a cap used as a medication reservoir connection interface apparatus.

FIG. 13 shows another embodiment of the present invention where an interface is provided to connect a reservoir to a conduit, such as tubing, via a standard luer fitting connection. This allows a luer style disposable infusion set to connect to the pump housing (not shown). A cap 46 is formed with a luer fitting 47 portion as an integral part thereof. Except for the shape of the luer fitting 47 portion, the cap 46 has all of the other features of the cap 12 shown in FIG. 5. Thus referring to FIG. 13, the cap 46 is comprised of, among other things, threads 19, detent openings 14, a shoulder 23, vent ports 24, a detent arm 34, and a needle (not shown) disposed in the interior of the cap 46.

While the embodiment of FIG. 13 includes a base member (not shown) to complete the connection of the cap 46 with a reservoir, other embodiments of the invention perform this function using a single integrated unit. In an illustrative embodiment shown in FIG. 15 which includes a number of typical elements of the invention, a luer adapter 51 is provided as a single, integral unit for connection to a standard prefilled cartridge or medication reservoir 52. The reservoir 52 is comprised of a watertight cylinder 53 having a neck 54 with an opening (not shown) at the proximate end of the cylinder 53. A swage 55 having an annular shoulder 56 is secured around the neck 54 of the cylinder 53. The swage 55 secures a rubber septum (not shown) over the opening (not shown) of the neck 54 thus providing a fluid-tight seal. The luer adapter 51 is comprised of a reservoir connector portion 57, a neck portion 58 and a male luer connector portion 59. The reservoir connector portion 57 includes a piercing member or needle 60 which is adapted to pierce the septum (not shown) of the reservoir 52 upon attaching it to the luer adapter 51.

In an illustrative embodiment shown in FIGS. 16A-16C which includes a number of typical elements of the invention, the reservoir connector portion 57 further comprises an open-ended cylindrical member 61 having a base 62 which closes one end of the cylindrical member 61. The needle 60 is enclosed by the cylindrical member 61 and projects axially from the base 62. The length of extension of the needle 60 from the base is shorter than that of the cylindrical member 61 which serves to protect the needle 60 and to reduce the likelihood of accidental needle contact with the hands of users.

Figure 15:
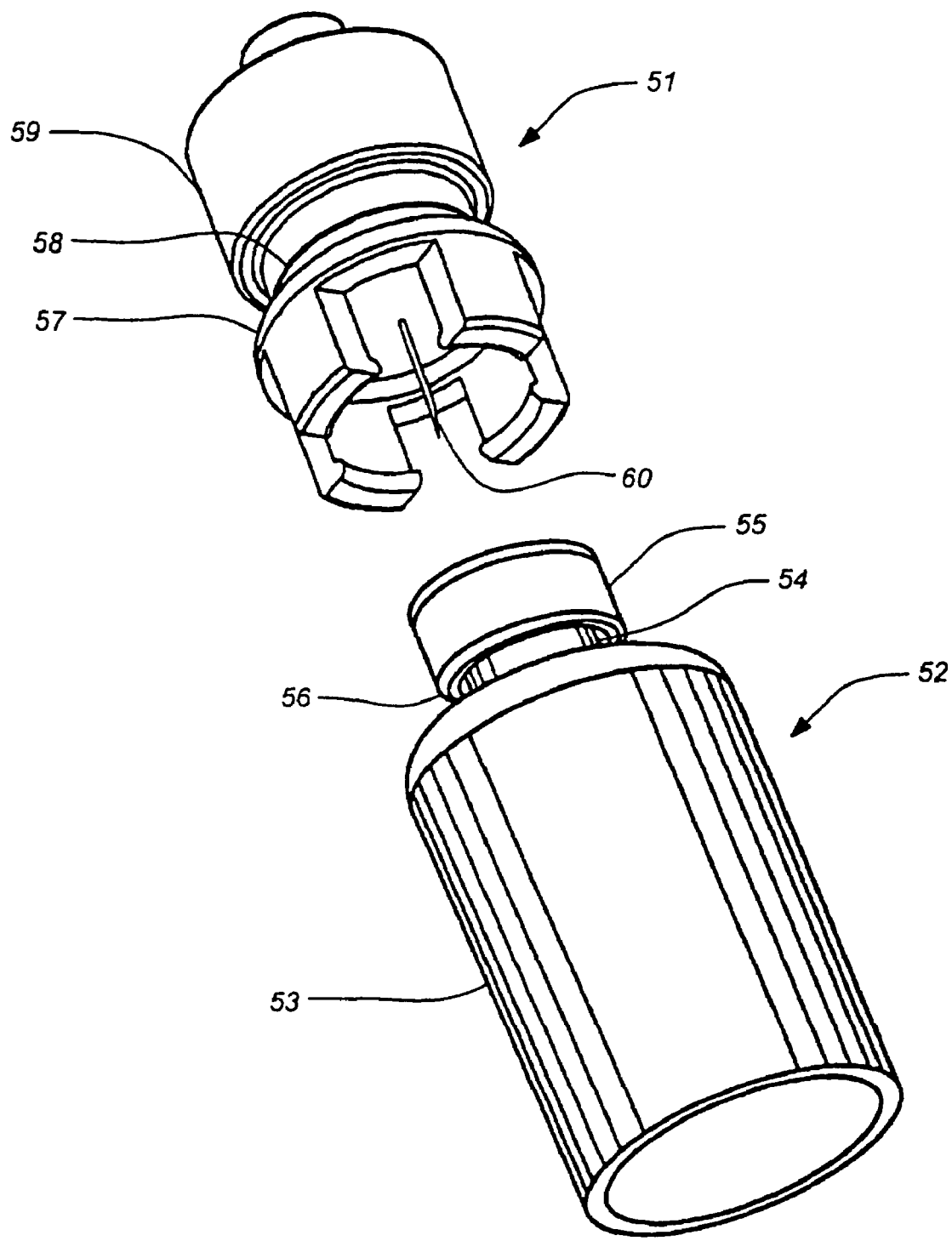
FIG. 15 is an exploded, perspective view of an embodiment of an integral medication reservoir connection apparatus and a reservoir.

In the embodiment of FIGS. 16A-16C, the cylindrical member 61 has a plurality of generally rectangular-shaped gaps 63 extending from the open end of the member 61 to the base 62 thereby forming a plurality of arms 64. To secure the luer adapter 51 to the reservoir 52, the arms 64 can be snapped over the reservoir swage 55 (FIG. 15). Inwardly protruding tabs 65 are formed on the end of the arms 64 and are sized to engage the annular shoulder 56 of the reservoir swage 55 thus securing it to the luer adapter 51 in a snap-fit engagement. Moreover, as the luer adapter 51 is inserted over the swage 55, the needle 60 pierces the reservoir septum thus providing a fluid path from the reservoir to the luer fitting.

The snap fit engagement disclosed herein allows a user to quickly and conveniently couple a reservoir to a specific interface, such as a luer, another snap-fit or any other fitting known in the art that is present on the conduit or device to which the reservoir is coupled. As used herein, snap-fit as in "snap-fit engagement" refers to the releasable coupling of a first member (e.g. the arm 64 of FIG. 16C) to a second member (e.g. the swage 55 in FIG. 15) where a protrusion on the first member (e.g. the tab 65 on the arm 64 of FIG. 16C) typically rides over a portion of the second member causing the first member to temporarily deflect until the protrusion on the first member is situated in a receiving space on the second member (e.g. the annular shoulder 56 of FIG. 15). Advantageously, this engagement typically results in a "click" when the first member is appropriately situated, thus providing both tactile and audible feedback to the user that the first member is securely engaged with the second member. Additional benefits of such an engagement include its facilitating a medical practitioner's ability to quickly and easily assemble an apparatus in situations where a patient requires immediate medical intervention.

Embodiments having a single integral unit comprising a base and a cap further reduce the amount of time needed to generate a fully functional medical device because there is no need to separately couple a base to a reservoir before using the adapter. In addition, because this embodiment comprises a single integral unit rather than a composite of multiple sub-units, this design facilites both operator handling as well as the maintenance of sterility. In addition, manufacturing is simplified because the device may be produced from a single mold.

In typical embodiment illustrated in FIGS. 16A-16C, the cylindrical member 61 is constructed of polyolefin or other material which has sufficient flexibility to permit the arms 64 to flex and snap fit over the reservoir swage 55 yet further has sufficient strength to secure the needle 60 in the luer adapter 51. Although the illustrative embodiment shown in FIGS. 16A-16C has arms 64, other embodiments of the present invention include an open-ended cylinder member which has no gaps in the cylinder wall and therefore no arms. Utilizing a material of appropriate flexibility, the cylinder member of such an embodiment is able to snap-fit over a reservoir swage. Furthermore, a balance may be struck between the flexibility (or elasticity) of the selected material and the number and dimensions (e.g. width and wall and tab thicknesses) of the arms 64 employed to obtain the design engagement feel. In embodiments for which the open-ended cylindrical member includes no arms, the wall and tab thicknesses are selected in consideration of the material elasticity.

In another typical embodiment of the invention that is illustrated in FIGS. 16A-16C the male luer connector portion 59 of the luer adapter 51 is joined to the reservoir connector portion 57 by the neck portion 58. The neck portion 58 is cylindrically-shaped and has a diameter which is smaller than that of the reservoir connector portion 57 as well as the male luer connector portion 59 of the luer adapter 51. The neck portion 58 is sized to fit within a housing of a medication infusion pump or any other apparatus so that the luer adapter 51 and reservoir 52 assembly can be secured therein. The male luer connector portion 59 is a standard fitting comprising a luer collar 66 and a luer taper 67.

Figure 17A:
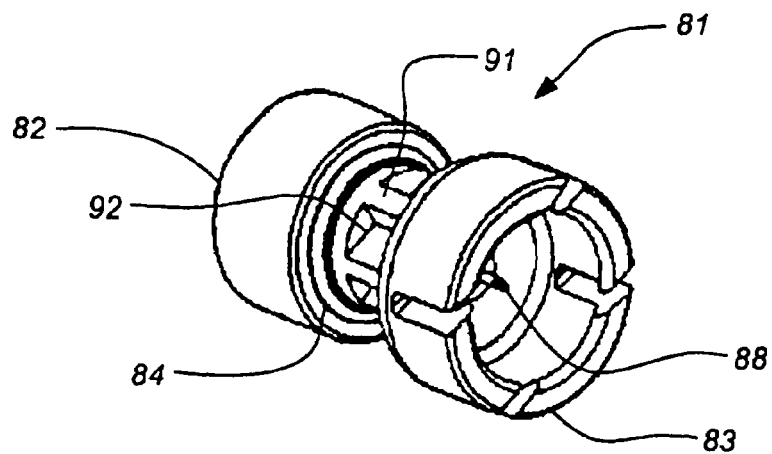
FIGS. 17A-17D are views of another embodiment of an integral medication reservoir connection embodiment.
Figure 17B:
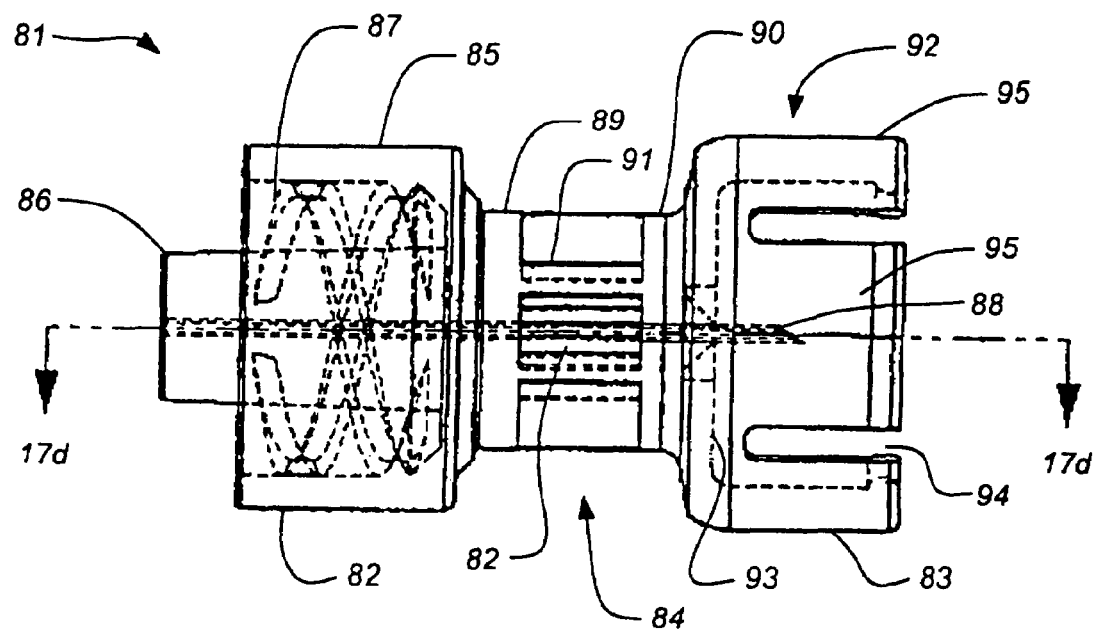

FIGS. 17A-17D show an another typical embodiment of an integral piece luer adapter 81. In this embodiment, the adapter 81, operates in essentially the same manner as the embodiment of FIGS. 16A-16C, and comprises a male luer connector portion 82 at one end, a reservoir connector portion 83 at the opposite end, and a connecting neck portion 84. The male luer connector portion 82 is a standard, known fitting which includes a luer collar 85, a luer taper 86 and threads 87 which are on the internal surface of the luer collar 85. As illustrated in FIG. 17B, the connecting neck portion 84 is generally cylindrical in shape and has a first collar 89 which attached to the male luer connector portion 82 as well as a second collar 90 which is attached to the reservoir connector portion 83. A plurality of longitudinally extending ribs 91 connect the first collar 89 with the second collar 90. A plurality of openings 92 which are defined by the ribs 91 expose a needle 88 which extends from the male luer connector portion 82, through the neck portion 84 and to the reservoir connection portion 83. The openings 92 provide access by external devices which can be used to grip the needle 88 during the assembly process. The needle 88 can be held in place while a mold is being filled during this assembly. Although a plurality of openings is preferred, only one such opening 92 is included to hold the needle 88.

Figure 17C:
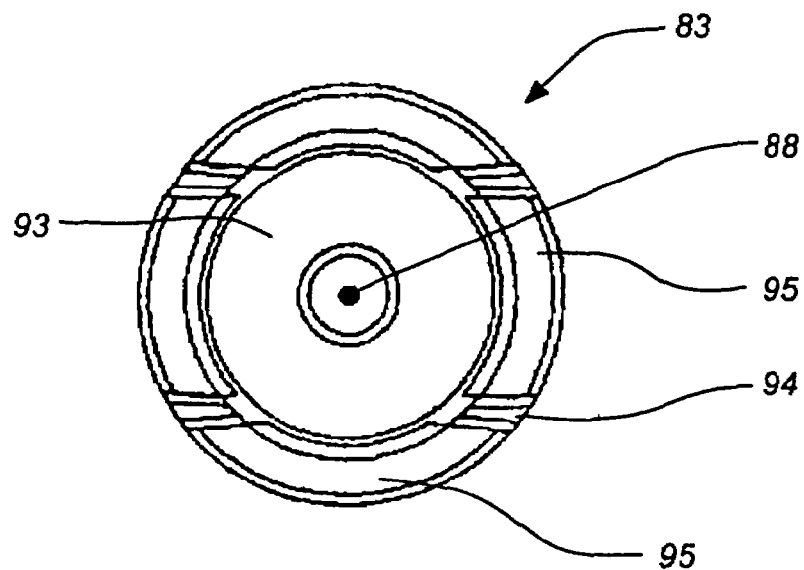
Figure 17D:
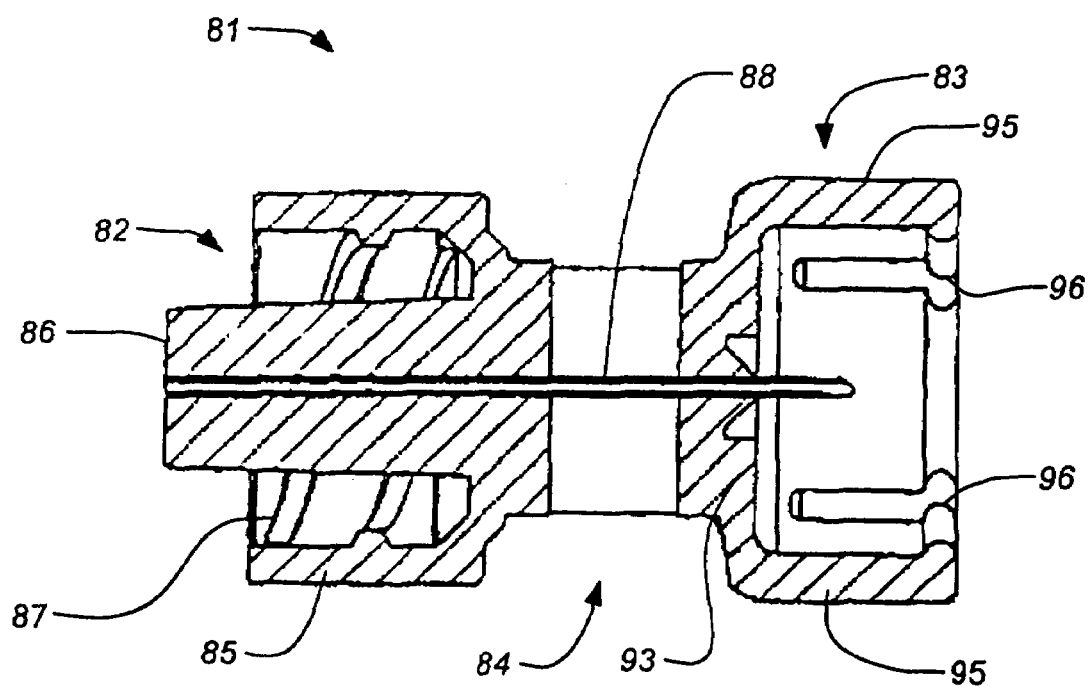

In the embodiment of the invention illustrated in FIGS. 17A-17D, the reservoir connector portion 83 comprises an open-ended cylindrical member 92 having a base 93 which closes one end of the cylindrical member 92. The needle 88 is enclosed by the cylindrical member 92 and projects axially from the base 93. The cylindrical member 92 has a plurality of generally rectangular-shaped gaps 94 extending from the open end of the member 92 to the base 93 thereby forming a plurality of arms 95. To secure the luer adapter 81 to a reservoir, the arms 95 can be snapped over a swage of an industry standard reservoir. As seen in FIG. 17D, inwardly protruding tabs 96 are formed on the end of the arms 95 and are sized to engage an annular shoulder of a standard reservoir swage thus securing it to the luer adapter 81 in a snap-fit engagement as previously described.

In the embodiment illustrated in FIGS. 17A-17D, the needle 88 projects axially from the base 93 of the cylindrical member 92 and extends for a length which is shorter than the length of the arms 95. The opposite end of the needle 88 extends to the end of the luer taper 86 thus providing a fluid flow path from a reservoir which may be attached to the reservoir connection portion 83 to infusion set tubing which may be attached to the luer connector portion 82. In one embodiment (not shown), the end of the needle 88 which extends to the luer taper 86 can be tapered outwardly in order to more securely seat the needle 88 in the luer adapter 81. Alternatively the needle 88 can be grit blasted in order to enhance the bonding to the body of the luer adapter 81, or the needle 88 can be assembled via an insertion molding process or an epoxy bonding process.

In another illustrative embodiment (not shown), the needle 88 does not extend to the end of the luer taper 86. Rather, the needle 88 terminates inside of the luer taper 86 and a cylindrical cavity (not shown) within the luer taper 86 extends from the end of the needle 88 to the exterior of the luer taper 86. This cavity can be sized to receive a needle or other conduit from another device in order to provide a flow path to refill a cartridge which may be attached to the reservoir connection portion 83.

As illustrated in FIGS. 17B and 17C, the arms 95 are wider and the gaps 94 are narrower than the arms 64 and the gaps 63 shown in the embodiment of FIGS. 16A-16C. As previously mentioned, the number and dimensions of the arms which are used to snap over the swage of a standard reservoir can be adjusted to accommodate the degree of flexibility of the material used to construct a cylindrical member portion of a luer adapter.

FIGS. 18A-18C show yet another embodiment of the present invention. In this embodiment, a luer adapter 101 is comprised of a reservoir connection portion 102 and a male luer connection portion 103. In contrast to the embodiments of FIGS. 16A and 17A, the luer adapter 101 does not have a neck portion since one may not be needed for those applications where it is not necessary for a luer adapter to be secured in a medication pump or other device in that fashion. However the luer adapter 101 does have a plurality of generally rectangular-shaped seating tabs 104 disposed on the reservoir connector portion 102. The tabs 104 can be used to secure the luer adapter 101 in a medication pump or other device housing. In other respects, the luer adapter 101 operates in the same manner as the embodiments of FIGS. 16A and 17A.

Those skilled in the art will appreciate that while the embodiments of FIGS. 15-18 disclose an adapter for connecting a standard reservoir to a luer fitting as a typical embodiment of the invention, the invention disclosed herein is not limited to luer fittings. Instead, the design of the inventive adapter can be used for connecting a standard reservoir to one or more of the variety of other types of fittings know in the art, such a swage or crimp fitting, threaded or unthreaded fittings, a nipple fitting or any other fitting known in the art without departing from the scope of the invention. By utilizing such a design, the invention therefore serves as a universal adapter for connecting elements such as a conduit to any one of a wide variety of reservoirs known in the art.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims rather than the foregoing description, and all changes which come within the meaning and range of equivalency of the claims are therefore intended to be embraced therein. All patents, patent application and literature references identified herein are incorporated herein by reference.

What is claimed is:

1. An apparatus for connecting a reservoir having a septum to a conduit; the apparatus comprising:
   a reservoir engagement member comprising a plurality of arms, a plurality of tabs or a cylindrical fitting; and
   a connector for connecting the apparatus to the conduit, wherein the connector comprises an open-ended cylindrical member adapted to receive a piercing member that is coupled to the conduit;
   wherein:
      the apparatus includes a housing engagement member comprising a tab or a thread disposed on the apparatus and adapted to engage an apparatus engagement member on a housing of a medication infusion pump so that the apparatus can be releasably secured within the housing of the medication infusion pump upon rotation of the apparatus by a user;
      the housing engagement member is positioned on the apparatus so that the apparatus and the reservoir are disposed within the housing of the medication infusion pump when the apparatus is secured within the housing; and
      the reservoir engagement member comprising the plurality of arms, the plurality of tabs or the cylindrical fitting, the connector comprising the open-ended cylindrical member and the housing engagement member are formed as a permanently integrated unit.

2. The apparatus of claim 1, wherein the housing engagement member comprises a tab.

3. The apparatus of claim 1, wherein the housing engagement member comprises a thread.

4. The apparatus of claim 1, wherein the reservoir engagement member flexibly deflects over a reservoir swage to engage the reservoir.

5. The apparatus of claim 1, wherein the reservoir-engagement member can be snapped over an annular shoulder of the reservoir to engage the reservoir.

6. The apparatus of claim 1, wherein the reservoir engagement member allows for a snap fit engagement with the reservoir.

7. The apparatus of claim 1, wherein engaging the reservoir results in a tactile feedback to a user when the apparatus is engaged with the reservoir.

8. The apparatus of claim 1, wherein engaging the reservoir results in a visual feedback to a user when the apparatus is engaged with the reservoir.

9. The apparatus of claim 1, wherein the piercing member pierces the reservoir septum when the conduit is connected with the apparatus and the apparatus is coupled and operatively engaged with the reservoir.

10. The apparatus of claim 1, wherein the open-ended cylindrical member is a luer connector.

11. The apparatus of claim 10, wherein the luer connector is a male luer connector.

12. The apparatus of claim 10, wherein the luer connector comprises a luer collar and a luer taper.

13. The apparatus of claim 1, wherein the apparatus is a single integral unit.

14. An apparatus for connecting a reservoir having a septum to a conduit; the apparatus comprising:
   engagement means adapted to engage the reservoir having the septum;
   a connector for connecting the apparatus to the conduit, wherein the connector comprises an open-ended cylindrical member; and
   means to receive a piercing member that is coupled to the conduit and adapted to pierce the septum of the reservoir;
   wherein;
      the apparatus includes a housing engagement means comprising a tab or a thread disposed on the apparatus and adapted to engage an apparatus engagement means on a housing of a medication infusion pump so that the apparatus can be releasably secured within the housing of the medication infusion pump upon rotation of the apparatus by a user;
      the housing engagement member is positioned on the apparatus so that the apparatus and the reservoir are disposed within the housing of the medication infusion pump when the apparatus is secured within the housing; and
   the engagement means, the connector comprising the open-ended cylindrical member, the means to receive a piercing member and the housing engagement member are formed as a permanently integrated unit.

15. The apparatus of claim 14, wherein the housing engagement means comprises a tab.

16. The apparatus of claim 14, wherein the housing engagement means comprises a plurality of rectangular-shaped tabs.

17. The apparatus of claim 14, wherein the engagement means adapted to engage the reservoir having the septum comprise a plurality of arms.

18. The apparatus of claim 17, wherein the plurality of arms can be snapped over an annular shoulder of the reservoir to engage the reservoir.

19. The apparatus of claim 17, wherein the plurality of arms allows for a snap fit engagement with the reservoir.

20. The apparatus of claim 14, engaging the reservoir results in a tactile feedback to a user when the apparatus is engaged with the reservoir.

21. The apparatus of claim 14, wherein engaging the reservoir results in a visual feedback to a user when the apparatus is engaged with the reservoir.

22. The apparatus of claim 14, wherein the piercing member pierces the reservoir septum when the conduit is connected with the apparatus and the apparatus is coupled and operatively engaged with the reservoir.

23. The apparatus of claim 14, wherein the open-ended cylindrical member is a luer connector.

24. The apparatus of claim 23, wherein the luer connector is a male luer connector.

25. The apparatus of claim 23, wherein the luer connector comprises a luer collar and a luer taper.

26. The apparatus of claim 14, wherein the apparatus is a single integral unit.

27. The apparatus of claim 14, further comprising a shoulder formed as part of the unit, wherein the shoulder is adapted to seat against the housing of the medication infusion pump to form a water tight seal.

28. The apparatus of claim 14, wherein the housing engagement member is disposed on the exterior of the apparatus.

29. A method of connecting a reservoir having a septum to a conduit, comprising the steps of:
   releasably coupling an apparatus to the reservoir having the septum, the apparatus comprising: a reservoir engagement member comprising a plurality of arms, a plurality of tabs or a cylindrical fitting and a connector for connecting the apparatus to the conduit, wherein the connector comprises an open-ended cylindrical member adapted to receive a piercing member that is coupled to the conduit; wherein the apparatus includes a housing engagement member comprising a tab or a thread disposed on the apparatus and adapted to engage an apparatus engagement member on a housing of a medication infusion pump so that the apparatus is adapted to be releasably secured within the housing of the medication infusion pump upon rotation of the apparatus by a user; and the reservoir engagement member comprising the plurality of arms, the plurality of tabs or the cylindrical fitting, the connector comprising the open-ended cylindrical member and the housing engagement member are formed as a permanently integrated unit;
   engaging the housing engagement member with the housing of the medication infusion pump and rotating the apparatus so as to secure the apparatus within the housing, wherein the apparatus and the reservoir are disposed within the housing of the medication infusion pump when the apparatus is secured within the housing; and
   connecting the conduit with the apparatus.

30. The method of claim 29, wherein the conduit is connected with the apparatus prior to connecting the apparatus to the reservoir having the septum.

31. The method of claim 29, wherein the housing engagement member comprises a tab.

32. The method of claim 29, wherein the engagement member adapted to engage the reservoir having the septum comprises a plurality of arms.

33. The method of claim 29, wherein engaging the reservoir results in a tactile or audible feedback to a user when the apparatus is engaged with the reservoir.

34. The method of claim 29, wherein the piercing member pierces the reservoir septum when the conduit is connected with the apparatus and the apparatus is coupled and operatively engaged with the reservoir.

35. The method of claim 29, wherein the open-ended cylindrical member is a luer connector.

36. The method of claim 35, wherein the luer connector is a male luer connector.

37. The method of claim 29, wherein the apparatus is a single integral unit.

38. The method of claim 29, wherein the apparatus further comprises a shoulder formed as part of the unit, wherein the shoulder is adapted to seat against the housing of the medication infusion pump to form a water tight seal.

39. The method of claim 29, wherein the housing engagement member is disposed on the exterior of the apparatus.

40. An apparatus for connecting a reservoir having a septum to a conduit; the apparatus comprising:
- a single circular reservoir engagement member adapted to engage a single cylindrical fluid medication reservoir and comprising a plurality of arms, a plurality of tabs or a cylindrical fining; and
- a connector for connecting the apparatus to the conduit, wherein the connector comprises an open-ended cylindrical member adapted to receive a piercing member that is coupled to the conduit;

wherein:
- the apparatus includes a housing engagement member comprising a tab or a thread disposed on the apparatus and adapted to engage an apparatus engagement member on a housing of a medication infusion pump so that the apparatus can be releasably secured within the housing of the medication infusion pump upon rotation of the apparatus by a user;
- the housing engagement member is positioned on the apparatus so that the apparatus and the reservoir are disposed within the housing of the medication infusion pump when the apparatus is secured within the housing; and
- the reservoir engagement member, the connector comprising the open-ended cylindrical member and the housing engagement member are formed as a permanently integrated unit.

41. The apparatus of claim 1, further comprising a shoulder formed as part of the unit, wherein the shoulder is adapted to seat against the housing of the medication infusion pump to form a water tight seal.

42. The apparatus of claim 40, further comprising a shoulder formed as part of the unit, wherein the shoulder is adapted to seat against the housing of the medication infusion pump to form a water tight seal.

43. The method of claim 40, wherein the housing engagement member is disposed on the exterior of the apparatus.

44. An apparatus for connecting a reservoir having a septum to a conduit; the apparatus comprising:
- a reservoir engagement member comprising a plurality of arms, a plurality of tabs or a cylindrical fitting; and
- a connector for connecting the apparatus to the conduit, wherein the connector comprises an open-ended cylindrical member adapted to receive a piercing member that is coupled to the conduit;
- wherein the apparatus includes a housing engagement member comprising a tab or a thread disposed on the exterior of the apparatus and adapted to engage an apparatus engagement member inside a housing recess of a medication infusion pump so that the apparatus can be releasably secured within the housing recess of the medication infusion pump upon rotation of the apparatus by a user, the apparatus and the reservoir at least partially fitting inside the housing recess of the medication infusion pump; and
- the reservoir engagement member comprising the plurality of arms, the plurality of tabs or the cylindrical fitting, the connector comprising the open-ended cylindrical member and the housing engagement member are formed as a permanently integrated unit.

* * * * *

UNITED STATES PATENT AND TRADEMARK OFFICE
CERTIFICATE OF CORRECTION

PATENT NO. : 7,628,772 B2  Page 1 of 1
APPLICATION NO. : 10/884609
DATED : December 8, 2009
INVENTOR(S) : McConnell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 393 days.

Signed and Sealed this

Second Day of November, 2010

David J. Kappos
*Director of the United States Patent and Trademark Office*